(12) United States Patent
Froggatt

(10) Patent No.: US 7,633,607 B2
(45) Date of Patent: Dec. 15, 2009

(54) METHOD AND APPARATUS FOR CALIBRATING MEASUREMENT EQUIPMENT

(75) Inventor: Mark Froggatt, Blacksburg, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 198 days.

(21) Appl. No.: 10/570,257

(22) PCT Filed: Sep. 1, 2004

(86) PCT No.: PCT/US2004/028273

§ 371 (c)(1),
(2), (4) Date: Dec. 11, 2006

(87) PCT Pub. No.: WO2005/024441

PCT Pub. Date: Mar. 17, 2005

(65) Prior Publication Data

US 2007/0171399 A1 Jul. 26, 2007

Related U.S. Application Data

(60) Provisional application No. 60/499,341, filed on Sep. 3, 2003.

(51) Int. Cl.
*G01N 21/00* (2006.01)
(52) U.S. Cl. .................. 356/73.1; 356/477
(58) Field of Classification Search .......... 356/73.1, 356/450, 477, 483; 385/11–12, 31–32, 34, 385/37
See application file for complete search history.

(56) References Cited

U.S. PATENT DOCUMENTS

| 5,268,741 | A | * | 12/1993 | Chou et al. | 356/479 |
| 5,298,972 | A | * | 3/1994 | Heffner | 356/364 |
| 5,721,615 | A | * | 2/1998 | McBride et al. | 356/477 |
| 6,069,697 | A | * | 5/2000 | Tanimoto et al. | 356/327 |
| 6,177,985 | B1 | * | 1/2001 | Bloom | 356/73.1 |
| 6,317,214 | B1 | * | 11/2001 | Beckett et al. | 356/477 |
| 6,449,033 | B2 | * | 9/2002 | Marro et al. | 356/73.1 |
| 6,813,028 | B2 | * | 11/2004 | Vanwiggeren | 356/477 |
| 6,856,400 | B1 | * | 2/2005 | Froggatt | 356/477 |

OTHER PUBLICATIONS

International Search Report for PCT/US04/28273 dated Aug. 3, 2005.

* cited by examiner

*Primary Examiner*—Sang Nguyen
(74) *Attorney, Agent, or Firm*—Nixon & Vanderhye P.C.

(57) ABSTRACT

Measurement equipment may be calibrated using two different calibration paths. An initial calibration is performed using a calibration path in which an optical element may be coupled for testing after the initial calibration. Once the initial calibration has been performed and the optical element operatively-connected in the main path for testing, one or more re-calibrations occur using another calibration path. The optical element being tested need not be de-coupled during the re-calibration. Each calibration operation produces error correction matrices which are used to correct the measurement matrix generated by the test equipment for the optical element being tested.

8 Claims, 20 Drawing Sheets

METHOD AND APPARATUS FOR CALIBRATING MEASUREMENT EQUIPMENT

This application is the US national phase of international application PCT/US2004/028273 filed 1 Sep. 2004, which designated the U.S. and claims priority to U.S. Provisional Application No. 60/499,341 filed 3 Sep. 2003, the entire contents of each of which are hereby incorporated by reference.

CROSS-REFERENCE TO RELATED APPLICATION

Priority is claimed under 35 U.S.C. §119(e) to commonly-owned, co-pending U.S. Provisional Patent Application Ser. No. 60/499,341, entitled "INTERNAL CALIBRATION METHOD AND APPARATUS," filed on Sep. 3, 2003, which is incorporated by reference.

TECHNICAL FIELD

The technical field relates to measurement or test equipment. In particular, the present invention relates to calibration of measurement or test equipment. One non-limiting, example application is to calibrating measurement equipment used to measure characteristics of or to test optical components.

BACKGROUND AND SUMMARY

Measurement equipment is important to the manufacture, sale, operation, and maintenance of modern electronic and optical devices and systems. A variety of measurement equipment is available such as vector analyzers, spectrum analyzers, power meters, etc. For purposes of illustration only, some of the following description is offered in the context of an optical vector analyzers (OVA), but the present invention is not limited to OVAs but applies to any suitable measurement device. One example OVA is described in commonly-assigned U.S. patent application Ser. No. 10/005,819, entitled "APPARATUS AND METHOD FOR THE COMPLETE CHARACTERIZATION OF OPTICAL DEVICES INCLUDING LOSS, BIREFRINGENCE AND DISPERSION EFFECTS," filed on Dec. 14, 2001, the disclosure of which is incorporated by reference. Most such measurement equipment allows for some sort of calibration in an attempt to remove the affect of measurement equipment errors from the measurement of a device under test (DUT). Typically, calibration involves testing a device having known characteristics which are compared to the measured characteristics in order to determine appropriate corrections or compensations to the measurement equipment output.

Consider fiber optic components as example DUTs. A fiber optic component can be accurately modeled using linear systems theory where a 2×2 complex matrix is used to represent a transfer function that characterizes the affect the fiber optic component has on light. If light passes through a series of components, the total transfer function is given by the product of these matrices.

$$\overline{E}_{out} = \overline{CBA}\overline{E}_{in} = \overline{X}\overline{E}_{in} \qquad (1)$$

This is illustrated in FIG. 1 which shows light $\overline{E}$ propagating through a series of optical components, each labeled with its corresponding matrix A, B, and C. The entire set of optical components can be represented as a single component matrix $\overline{X}$ that encompasses all of the properties of the individual components, as shown in FIG. 2.

Measurement equipment (like an OVAs) typically determines a matrix corresponding to the transfer function for an individual optical DUT. See for example the illustration in FIG. 3. Such a matrix may be, for example, a Jones matrix. The connections from the measurement equipment 10 to the DUT 12 and optical components within or otherwise associated the measurement equipment (hereafter "internal optics") affect the light, and thus, the accuracy of the measurement matrix. These connections and internal optics occur at both the input and the output of the measurement equipment. A "real" measurement equipment can be represented using an ideal (perfect) measurement equipment with source and detector error matrices, D (14) and S (16), as shown in FIG. 4.

If the source and detector error matrices, D and S, can be determined, they can be inverted and used to operate on the measured DUT matrix, M, to find a corrected matrix $M_c$:

$$M_c = D^{-1}MS^{-1} = D^{-1}DXSS^{-1} = X \qquad (2)$$

$M_c$ is an accurate measurement of the device, free of the errors created by imperfect measurement equipment and connectors. The source and detector error matrices can be determined if the Device Under Test (DUT) is replaced with a device R known to be free of loss and significant dispersion, e.g., a short section of optical fiber. Although a short fiber is essentially lossless, mild bends in the fiber can cause the fiber section to change the polarization state of the light. The lossless transfer function matrix that corresponds to the fiber section is commonly known as a "rotation" matrix R, which is illustrated in FIG. 5.

Because the rotation matrix R is lossless, there can not be any change in loss for different input polarization states to the fiber section. In other words, the fiber section has zero Polarization Dependent Loss (PDL). If the fiber section is connected to the imperfect measurement equipment, and the inverted source and detector error correction matrices ($D^{-1}$ and $S^{-1}$) are applied to the output produced by the measurement equipment, then the output should be lossless. If the inverted source and detector error correction matrices ($D^{-1}$ and $S^{-1}$) are correct, a lossless matrix will result for all rotational matrices R. In other words, if the fiber connecting the source to the detector is re-oriented, there will still be zero PDL and zero insertion loss produced by the fiber section.

The product of two rotational matrices is always a rotational matrix. Further, multiplication of any matrix by a rotation matrix will not change its PDL or insertion loss characteristics. This is similar to a situation where adding a length of fiber (or cutting off a length of fiber) from a component lead does not change the component's PDL or insertion loss. Therefore, if the inverted source and detector error matrices are multiplied by rotational matrices, the measured PDL or insertion loss of the device being measured will not change.

The transfer matrix of the lossless fiber section at three different orientations or polarizations produces three measured matrices:

$$\overline{M}_0 = \overline{D}\overline{R}_0\overline{S}, \qquad (3)$$

$$\overline{M}_1 = \overline{D}\overline{R}_1\overline{S}, \text{ and} \qquad (4)$$

$$\overline{M}_2 = \overline{D}\overline{R}_2\overline{S}. \qquad (5)$$

From these three measured matrices, the following detector and source correction matrices can be determined:

$$\overline{D}' = \overline{R}_D\overline{D}^{-1}, \text{ and} \qquad (6)$$

$$\overline{S}' = \overline{S}^{-1}\overline{R}_s. \qquad (7)$$

The process by which these detector and source correction matrices $\overline{D}'$ and $\overline{S}'$ are determined from the three measurements $\overline{M}_0$, $\overline{M}_1$, and $\overline{M}_2$, which were made by an imperfect measurement system of three lossless rotation matrices, is referred to as the "Basic Calibration Algorithm (BCA)," and is set forth below:

$$BCA_S(\overline{M}_0,\overline{M}_1,\overline{M}_2)=\overline{S}'=\overline{S}^{-1}\overline{R}_S \quad (8)$$

$$BCA_D(\overline{M}_0,\overline{M}_1,\overline{M}_2)=\overline{D}'=\overline{R}_D\overline{D}^{-1} \quad (9)$$

where $BCA_S$ is the basic calibration algorithm for calculating the source error correction matrix $\overline{S}'$, and $BCA_D$ is the basic calibration algorithm for calculating the detector error correction matrix $\overline{D}'$.

That process is as follows. Define a new intermediate matrix, $\overline{Y}$, as the inverse of $\overline{M}_0$, $\overline{Y}=\overline{M}_0^{-1}$. Calculate the eigenvectors of the product of $\overline{Y}$ and $\overline{M}_1$ and assemble these into an eigen-matrix, $\overline{E}$, that can be used to diagonalize $\overline{M}_1\overline{Y}$. The relative amplitudes of the eigenvectors are chosen such that $$\overline{E}^{-1}\overline{M}_1\overline{Y}\overline{E} = \begin{bmatrix} e^{-\varphi_1} & 0 \\ 0 & e^{-\varphi_2} \end{bmatrix}.$$

This matrix is "diagonal" because the off-diagonal entries are zero. The matrix is also lossless because the magnitude of the entries on the diagonal is unity. Therefore, the matrix also has zero PDL and satisfies the criteria of correcting for PDL effects in the detector matrix, $\overline{D}$. A detailed description of the calculation of eigenvectors and their application to diagonalizing matrices can be found in "*Elementary Linear Algebra*," by Howard Anton (John Wiley and Sons, New York).

There is a family of matrices that will diagonalize $\overline{M}_1$ and produce unity amplitude entries. In other words, the eigen-matrix, $\overline{E}$, is only one solution. Therefore, although $\overline{E}$ will properly diagonalize $\overline{M}_1\overline{Y}$, and $\overline{M}_0\overline{Y}$, $\overline{E}$ is not fully determined. We can create another matrix, $\overline{W}$, which has the property that it diagonalizes both $\overline{M}_1\overline{Y}$ and $\overline{M}_0\overline{Y}$, and yet has an additional degree of freedom. This matrix, $\overline{W}$, is created by multiplying the eigenmatrix, $\overline{E}$, by a matrix having PDL, but no off-diagonal terms:

$$\overline{W} = \overline{E}\begin{bmatrix} r & 0 \\ 0 & \frac{1}{r} \end{bmatrix}, \text{ where,} \quad (10)$$

$$\overline{W}^{-1} = \begin{bmatrix} \frac{1}{r} & 0 \\ 0 & r \end{bmatrix}\overline{E}^{-1}, \quad (11)$$

$$\overline{W}^{-1}\overline{M}_1\overline{Y}\overline{W} = \begin{bmatrix} e^{-\varphi_1} & 0 \\ 0 & e^{-\varphi_2} \end{bmatrix}, \quad (12)$$

and $$\overline{W}^{-1}\overline{M}_0\overline{Y}\overline{W} = \begin{bmatrix} 1 & 0 \\ 0 & 1 \end{bmatrix}. \quad (13)$$

If we apply this correction to the matrix formed by the product of $\overline{M}_2$ and $\overline{Y}$, i.e., $\overline{M}_2\overline{Y}$, in order to correct for the errors induced by the detector matrix, we get:

$$\overline{W}^{-1}\overline{M}_1\overline{Y}\overline{W} = \begin{bmatrix} \frac{1}{r} & 0 \\ 0 & r \end{bmatrix}\overline{E}^{-1}\overline{M}_2\overline{Y}\overline{E}\begin{bmatrix} r & 0 \\ 0 & \frac{1}{r} \end{bmatrix} \quad (14)$$

A search algorithm can be used to determine the value of the real-positive number, r, such that the polarization dependent loss of the entire matrix, $\overline{W}^{-1}\overline{M}_1\overline{Y}\overline{W}$, is zero.

We now have two matrices that can be used to correct for the errors induced by the source and detector matrices. Given an arbitrary measurement, $\overline{X}$, containing the effects of the source and detector matrix, these errors can be removed by applying the matrices as below:

$$\overline{X}_{corrected}=\overline{W}^{-1}\overline{X}\overline{Y}\overline{W}=\overline{D}'\overline{X}\overline{S}' \quad (15)$$

where we now see that, $$\overline{D}'=\overline{W}^{-1}=\overline{D}\overline{R}_D, \quad (16)$$

and $$\overline{S}'=\overline{Y}\overline{W}=\overline{S}\overline{R}_S. \quad (17)$$

The two unknown rotation matrices $R_D$ and $R_S$ are equivalent to a fiber section connected to the measurement equipment, and as a result, have no affect on the DUT measurement. So equations (6) and (7) permit calculation of the inverted detector and source error matrices that allow determination of the DUT corrected matrix $M_c$, as defined in equation (2). This is illustrated in FIG. 6.

When conducting tests of optical DUTs, such as wavelength filters and dispersion compensators, it is advantageous to be able to remove the source and detector errors from the DUT measurement using properly determined source and detector error matrices. The source and detector error matrices may be determined by connecting the lossless calibration device between the source and detector connectors, measuring the three different rotation matrices, and then calculating the source and detector error matrices, as described above.

FIG. 7 shows a fiber-loop polarization controller 20 connected between the source and detector. The fiber-loop polarization controller is adjusted to three different polarizations, e.g., by moving "paddles" of the fiber-loop polarization controller to three distinct positions to obtain the three distinct measurement matrices $M_0$-$M_2$. The three measurement matrices $M_0$-$M_2$ may be determined using a quarter-wave fiber loop positioned at each of 0°, 45°, and 90°. From $M_0$-$M_2$, the source and detector error correction matrices may be calculated.

A significant drawback with this calibration method is that the device under test must be disconnected from the measurement equipment in order to re-calibrate the measurement equipment. Such re-calibration is often necessary because characteristics of optical components internal to the measurement equipment often "drift." This drift is primarily caused by thermal changes, and a change of 0.5° Celsius can cause the measurement equipment to drift out of calibration. As a result, re-calibration of the internal components must be carried out frequently. This frequent re-calibration is problematic because the device under test must be disconnected every re-calibration.

The present invention overcomes this significant problem by providing another calibration path referred to as a "re-calibration path." The re-calibration path may include a fiber-loop polarization controller. In one non-limiting example, the re-calibration path could be internal to the test equipment, but it may also be external. The re-calibration path is distinct from the "main calibration path," and advantageously, the re-calibration may occur after the initial, main calibration and without having to disconnect the device under test.

Another inventive feature relates to the measurement equipment source and detector connectors for connecting the device under test to the test equipment. Those connectors may not be included in the re-calibration calculations. But because these connectors can influence the calibration, e.g., they can add as much as a 0.07 dB error to both PDL and insertion loss, the connectors should be accounted for in some way in the re-calibration. Fortunately, the source and detector connector characteristics do not drift much with time or with temperature, so they need not be re-calibrated often. Thus, once the source and detector connector calibrations are initially determined during the main calibration, they can be re-used with the re-calibration results to provide new correction matrices.

With the main initial calibration and one or more re-calibrations, the DUT may remain connected and accurately measured for long periods of time. This is a significant advance for measurement equipment.

Certain aspects of the invention will now be described in accordance with certain features recited in certain claims. One aspect relates to a method for calibrating apparatus for measuring one or more characteristics of an optical element. A calibration operation is performed using a first calibration path without the optical element having to be operatively-decoupled from the apparatus. The optical element to be tested may be coupled for testing between the source connector and a detector connector of the apparatus. A second calibration operation may also be performed, (typically before device testing), using a second calibration path. But when performing the second calibration, the optical element is operatively decoupled from the apparatus.

The first calibration path may include a fiber-loop polarization controller that remains in the first calibration path even when the optical element under test is coupled to the apparatus. That polarization controller operates as a rotation matrix during the first calibration operation. The first polarization controller is moved to multiple positions, and one or more first calibration corrections is determined for the apparatus at each of the multiple positions. The first calibration corrections are then used to update the calibration initially performed.

More specifically, the calibration includes determining a source correction matrix that corrects for an affect of one or more optical components coupled between a light source in the apparatus and a source connector. A detector correction matrix is also determined that corrects for an effect of one or more optical components coupled between a light detector in the apparatus and a detector connector. During testing, a DUT is operatively-coupled to these connectors. The first calibration operation includes determining an optical transfer function through the fiber loop polarization controller at multiple positions. The source and detector correction matrices are then determined using the optical transfer functions determined at each of the multiple positions.

In a non-limiting example embodiment, the first calibration corrections do not account for the source and detector connectors. Accordingly, the re-calibration uses the source and detector error correction matrices from the first calibration operations and combines them with the corrections for the source connector and error detector initially determined during the second calibration operation. A controller switches optical switches to select either the first calibration path or the second calibration path. Single port and multi-port/multi-channel implementations are described.

DETAILED DESCRIPTION

The following description sets forth specific details, such as particular embodiments, procedures, techniques, etc., for purposes of explanation and not limitation. But it will be appreciated by one skilled in the art that other embodiments may be employed apart from these specific details. For example, although the following description is facilitated using non-limiting examples, the present invention may be employed in any measurement equipment. In some instances, detailed descriptions of well-known methods, interfaces, circuits, and signaling are omitted so as not obscure the description with unnecessary detail. Moreover, individual blocks are shown in some of the figures. Those skilled in the art will appreciate that the functions of those blocks may be implemented using individual hardware circuits, using software programs and data, in conjunction with a suitably programmed digital microprocessor or general purpose computer, using application specific integrated circuitry (ASIC), and/or using one or more digital signal processors (DSPs).

Figure 8:
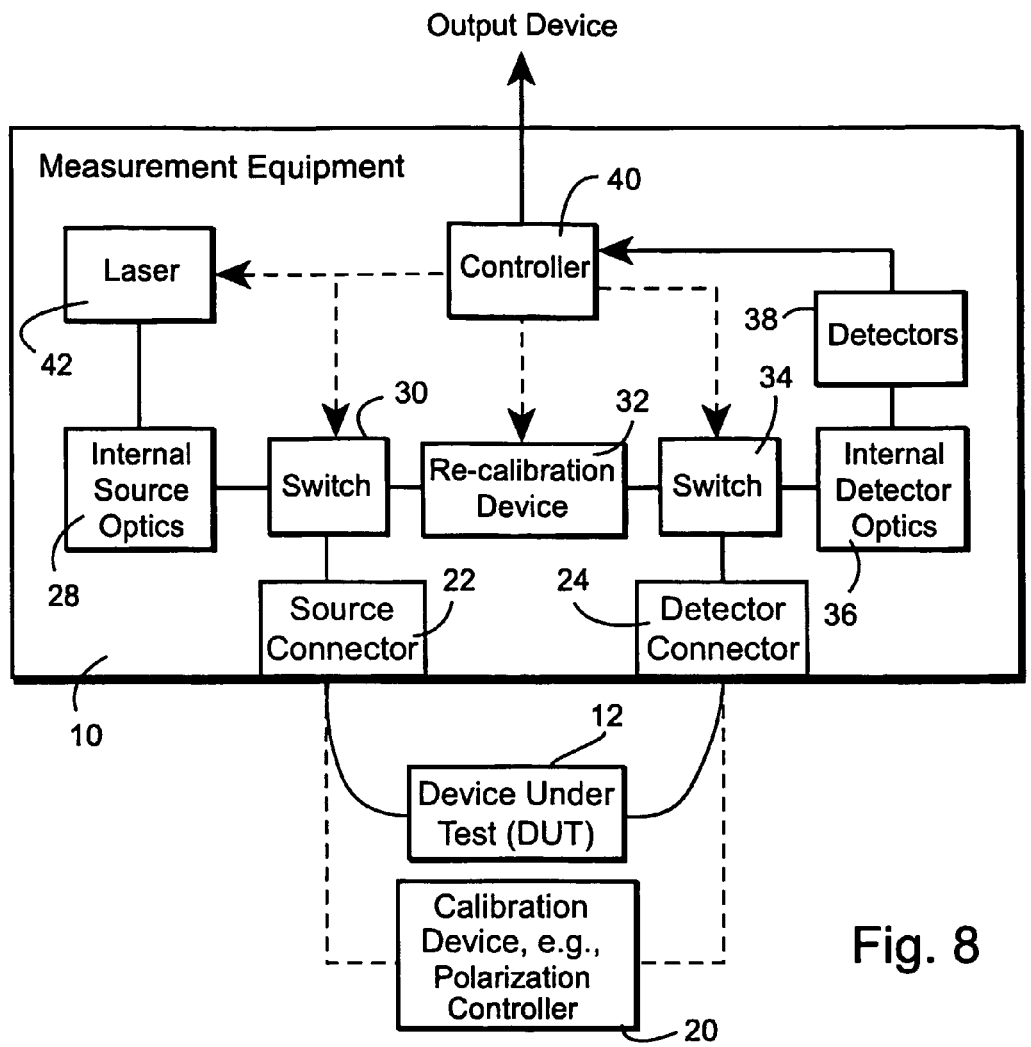
FIG. 8 illustrates measurement equipment that includes main calibration path and a re-calibration path.

FIG. 8 discloses a measurement device 10 that includes a laser 42 coupled to internal "source" optics 28 such as optical splitters, couplers, circulators, isolators, switches, polarization controllers, etc. that have an associated internal source error. The internal source optics are coupled to a first switch 30 controlled by a controller 40. The output of the switch 30 in a test position is coupled to the source connector (S) 22, and in a re-calibrate position, to a lossless re-calibration element 32, e.g., a polarization controller. The DUT 12 may be operatively coupled between the source connector (S) 22 and a detector connector (D) 24 for testing. The detector connector 24 is coupled to a second switch 34 controlled by the controller 40. The detector connector 24 is also coupled to internal detector optics 36, such as wavelength filters, optical couplers, polarization beam-splitters, switches, polarization controllers, quarter-wave plates, half-wave plates, polarizers, etc., that process the received optical signal before it is detected at optical detectors 38, e.g., photodiodes. The detector 38 output is coupled to the controller 40 which processes the output at each scanned laser wavelength in accordance with the procedures and mathematical equations described below. The processing results may be output to a display, printer, or other device if desired. When the switches 30 and 34 are switched to the re-calibrate path position, the internal source optics 28 and internal detector optics 36 are coupled via a re-calibration device 32, e.g., a lossless fiber loop or polarization controller.

Initially, the measurement equipment is calibrated over the re-calibration path. The switches 30 and 34 are each coupled to the re-calibration device (32), which is a lossless polarization controller. The polarization controller (32) is adjusted to three different polarization positions 0°, 45°, and 90°. At each position, three measurement matrices are determined by the controller based on the light detected at the detectors 38: $M_0$, $M_1$, and $M_2$. The three main calibration path measurement matrices $M_0$-$M_2$ are then used by the controller 40 along with the Basic Calibration Algorithms to determine a source error correction matrix, $\overline{S}'$, corresponding to effects in the relatively unstable internal source optics (28) and a detector error calibration matrix, $\overline{D}'$, corresponding to effects in the relatively unstable internal detector optics 36. Those error correction matrices are then used to correct subsequent measurements for the effects of the large and variable internal optics errors.

Next, the main path is calibrated. This calibration is carried out with a calibration device 20 connect from the source connector 22 to the detector connector 24. The calibration device is typically a lossless polarization controller that can be constructed using optical waveplates or optical fiber loops. Switch 30 is set to connect the internal source optics to the source connector 22, and switch 34 is set to connect the internal detector optics to the detector connector 24. Three measurements are then made at three different positions of the polarization controller 20. The source, $\overline{S}'$, and detector, $\overline{D}'$, correction matrices determined using the re-calibration path as described above are applied to this second set of measurement matrices in order to remove the effects of the internal source optics 28 and the internal detector optics 34. This second set of measured matrices are then used to remove the effects of the source connector 22 and the detector connector 24.

Figure 9:
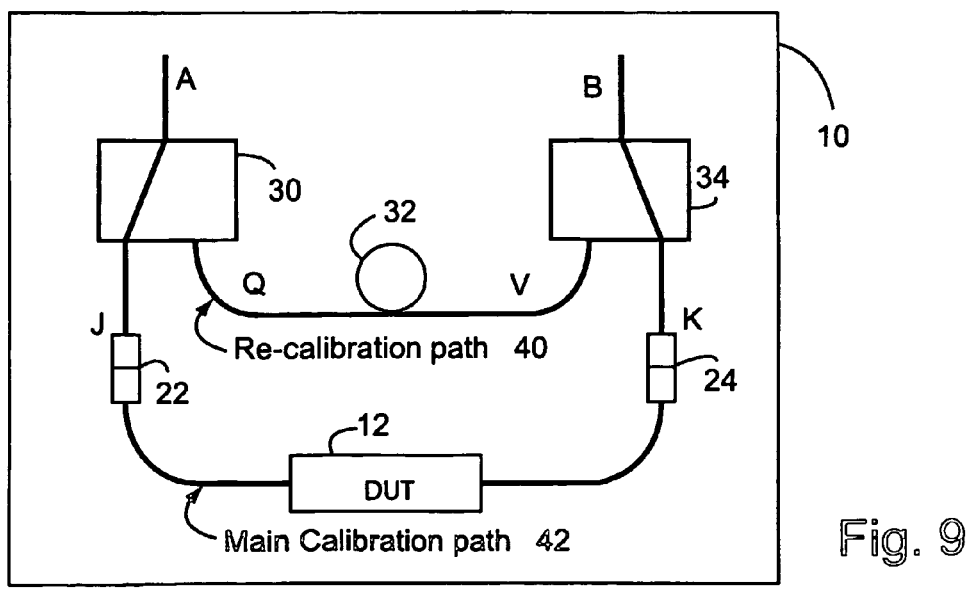
FIG. 9 is a network calibration model in which both a main calibration path and re-calibration path are employed.

The calibration is now explained in further detail in conjunction with FIG. 9. Each of the matrices contributing to the errors in the measurement system is labeled. The matrix, $\overline{A}$, corresponds to the transfer function representing internal source optics 20, and the matrix, $\overline{B}$, corresponds to the transfer function representing the internal detector optics 36. These two matrices, $\overline{A}$ and $\overline{B}$, contain the effects of most of the optical elements in the system, and as a result, are the least stable and contain the largest errors. The matrix, $\overline{J}$, corresponds to the transfer function representing the effects of the source connector 22 as well as the effects of the switch 30 that are specific to the side of the switch 30 connected to the source connector 22. Similarly, the matrix, $\overline{K}$, corresponds to the transfer function representing the effects of the detector connector 24 as well as the effects of the switch 34 that are on the side of the switch 34 connected to the detector connector 24. The matrix, $\overline{Q}$, represents any effects of the switch 30 when it is connected to the re-calibration path 32. Matrix, $\overline{V}$, represents any effects of the switch 34 when it is connected to the re-calibration path 32. The inclusion of matrices $\overline{Q}$ and $\overline{V}$ means that no presumption about the quality of the switch has been made other than its repeatability. In other words, significant PDL in the switch is acceptable, as long as it is repeatable.

Figure 1:
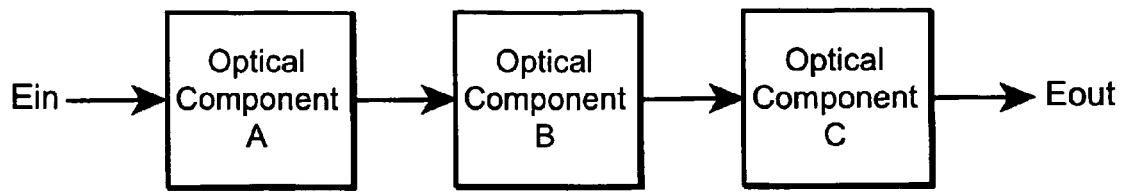
FIG. 1 is a diagram illustrating light propagation through a series of optical components.
Figure 2:
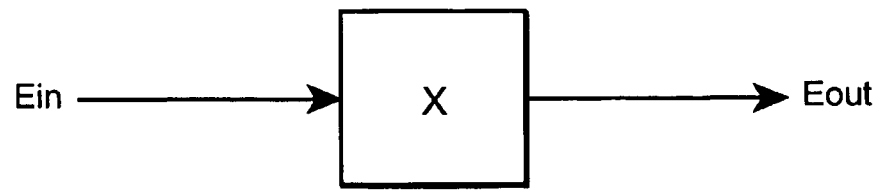
FIG. 2 is a diagram of a system equivalent to FIG. 1 where the series of optical components has been combined into a single component.
Figure 3:
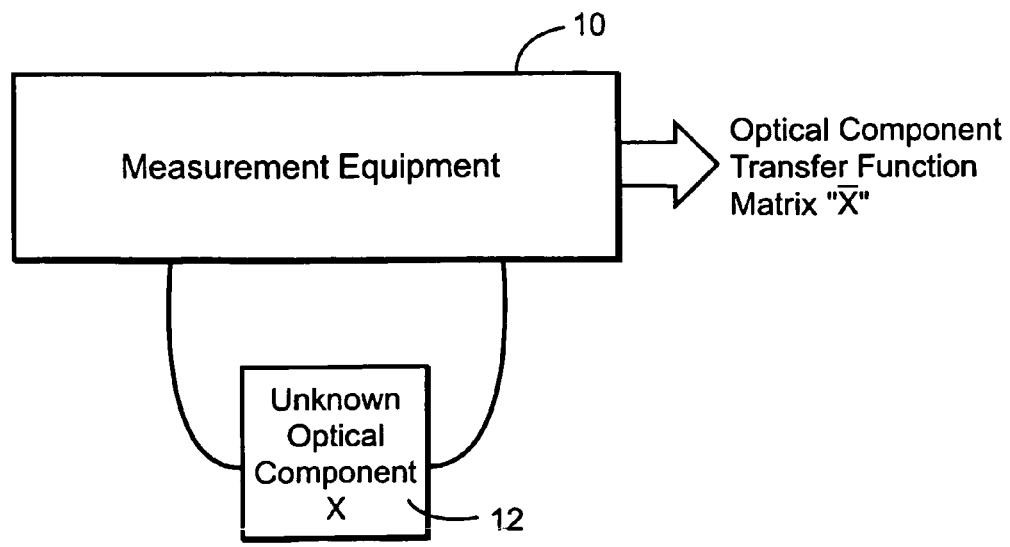
FIG. 3 is a diagram illustrating an ideal measurement system coupled to an unknown optical component.
Figure 4:
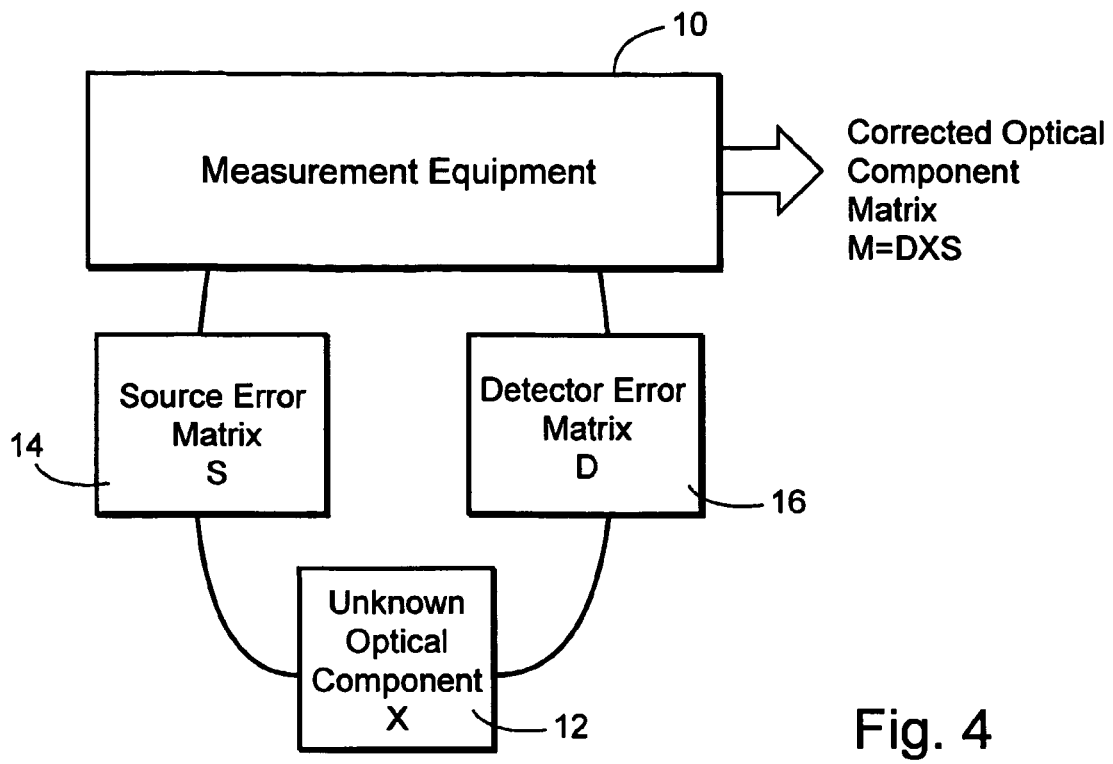
FIG. 4 is a diagram of a practical measurement system connected to an unknown optical component X.
Figure 5:
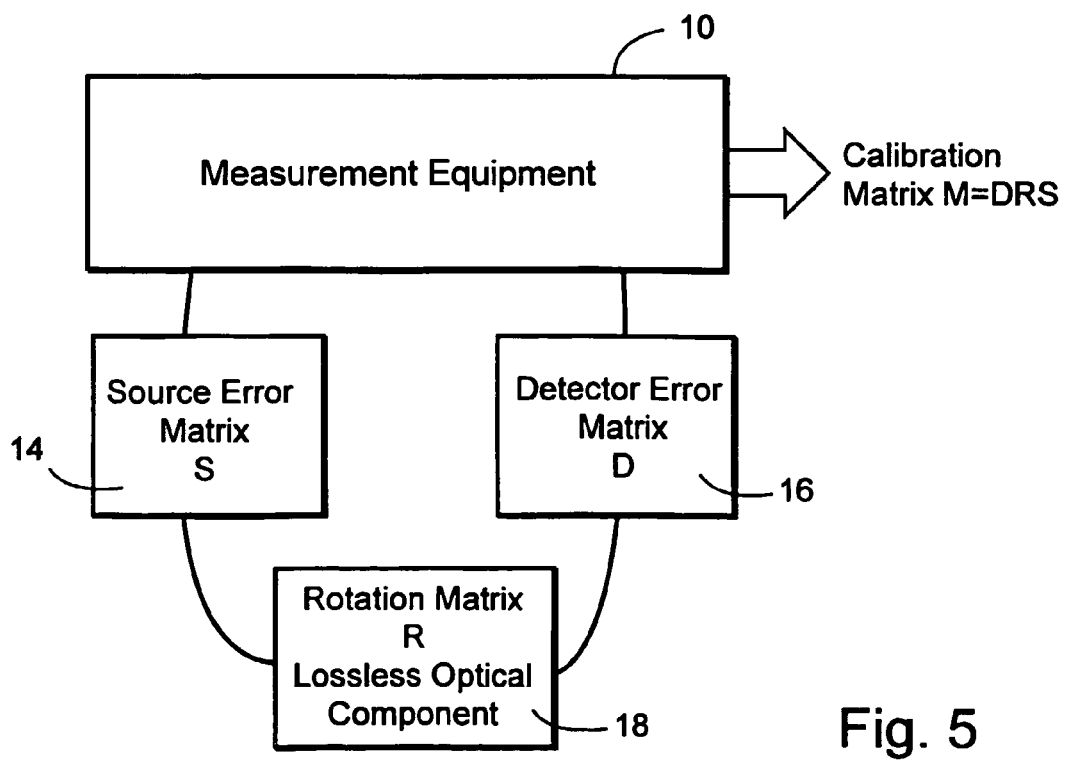
FIG. 5 is a diagram of a measurement system coupled to a known, lossless optical component for calibration.
Figure 6:
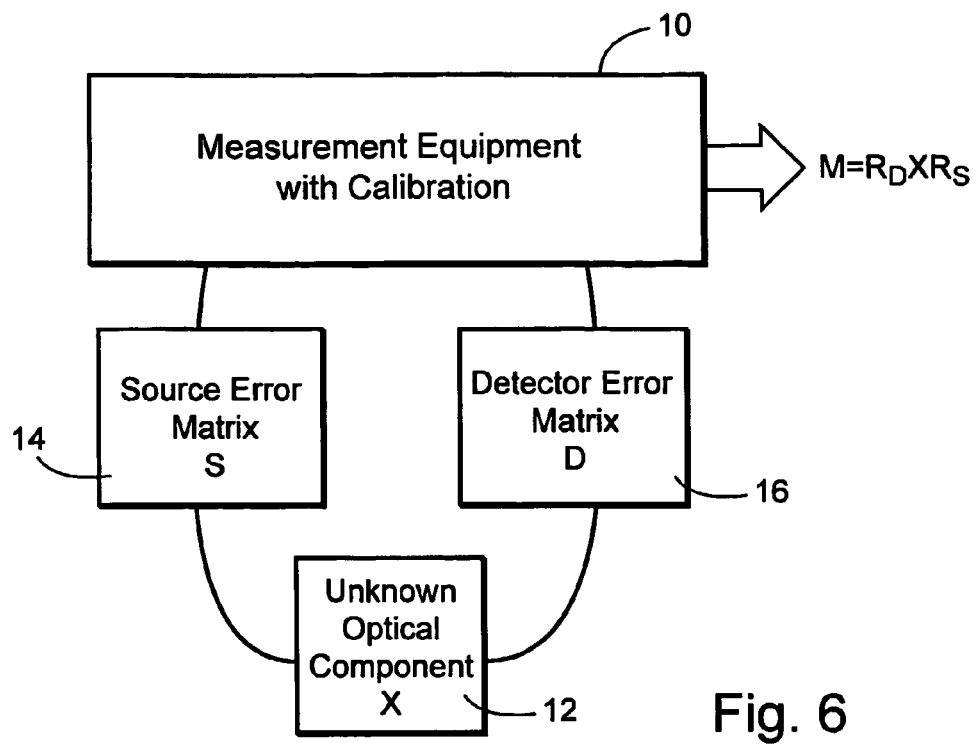
FIG. 6 illustrates a measurement equipment coupled to unknown optical component X.
Figure 7:
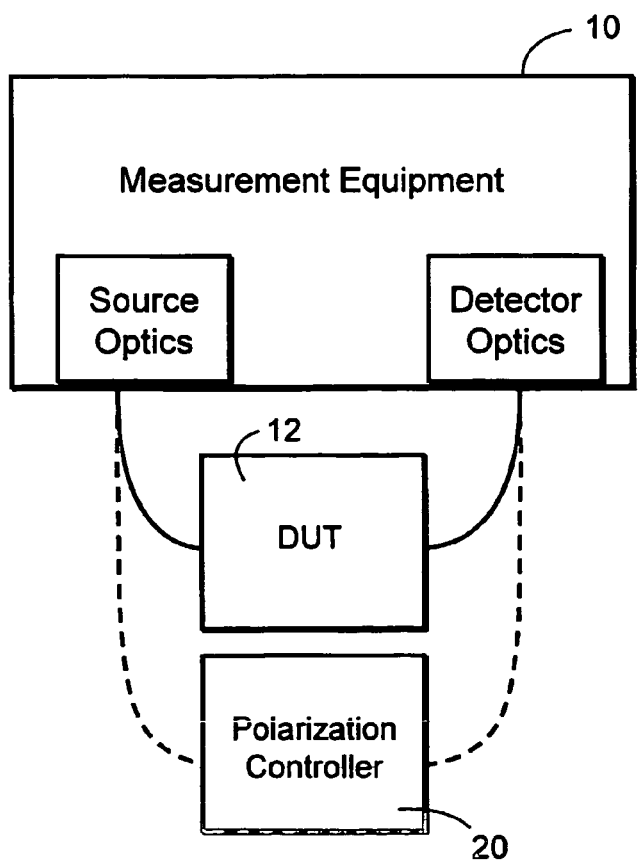
FIG. 7 illustrates measurement equipment selectively coupled to a device under test and to a polarization controller.

In the context of FIG. 5 and the above analysis describing the Basic Calibration Algorithms, the source matrix is, $\overline{JA}$, and the detector matrix is $\overline{BK}$. Therefore, we need a process that will find, $\overline{A}^{-1}\overline{J}^{-1}\overline{R}_{AJ}$, and $\overline{R}_{KB}\overline{K}^{-1}\overline{B}^{-1}$. Further, if the internal source optics 28 and/or the internal detector optics 36 change due to environmental fluctuations or other causes to produce new and different effects given by $\overline{A}_{drift}$ and $\overline{B}_{drift}$, we would like to be able to find $\overline{A}_{drift}^{-1}\overline{J}^{-1}\overline{R}_{AJ}$ and $\overline{R}_{KB}\overline{K}^{-1}\overline{B}_{drift}^{-1}$ using only the re-calibration path without disconnecting or disturbing any DUT that may be currently connected to the source connector 22 and the detector connector 24.

Reference is made to FIG. 9 which illustrates a re-calibration path 40 in parallel with the main calibration path 42 and a DUT 12 connected to the source and detector connectors 22 and 24. If the measurement equipment includes an OVA, the re-calibration path 40 may be internal to the OVA or external to the OVA. The model includes error matrices A, B, Q, V, J, and K. Error matrices A and B correspond to the internal source and detector optics, Q and V to sections of the re-calibration path, and J and K to the source and detector connectors.

The goal is to remove the polarization and insertion loss and other errors introduced by the error causing matrices from subsequent measurements and to specifically correct for any changes that may occur in A or B. Error matrices A and B represent the more complicated internal optical paths and components that are subject to thermal drift. The re-calibration polarization controller 32 is set to three different polarization positions 0°, 45°, and 90° at which three corresponding measurements are made with the measurement equipment 10 that produce three measurement matrices $M_0$, $M_1$, and $M_2$ as follows:

$$\overline{M}_0 = \overline{BVR}_0\overline{QA} \tag{18}$$

$$\overline{M}_1 = \overline{BVR}_1\overline{QA} \tag{19}$$

$$\overline{M}_2 = \overline{BVR}_2\overline{QA} \tag{20}$$

where $\overline{R}_0$ is an arbitrary lossless rotation matrix.

These three measurements can then be used by the Basic Calibration Algorithm (described above) to produce source, $\overline{S}'$, and detector, $\overline{D}'$, correction matrices. In this case, the source matrix is given by $\overline{QA}$, and the detector matrix is given by $\overline{BV}$. The calculated matrices are then:

$$BCA_S(\overline{M}_0,\overline{M}_1,\overline{M}_2) = BCA_S(\overline{BVR}_0\overline{QA},\overline{BVR}_1\overline{QA},\overline{BVR}_2\overline{QA}) = \overline{S}' = \overline{A}^{-1}\overline{Q}^{-1}\overline{R}_{AQ} \tag{21}$$

and $$BCA_D(\overline{M}_0,\overline{M}_1,\overline{M}_2) = BCA_D(\overline{BVR}_0\overline{QA},\overline{BVR}_1\overline{QA},\overline{BVR}_2\overline{QA}) = \overline{D}' = \overline{R}_{VB}\overline{V}^{-1}\overline{B}^{-1}. \tag{22}$$

We now have correction matrices for our most variable components: the internal source optics 28, $\overline{A}$, and the internal detector optics 36, $\overline{B}$. However these corrections matrices provide no corrections for the more stable effects of the source connector 22, $\overline{J}$, and the detector connector 24, $\overline{K}$. Further, they contain corrections for effects of the switches 30 and 34 when they are connected to the re-calibration path. The effects can be properly accounted for by calibrating the main path.

The DUT is replaced by a polarization controller, and three measurements are made at three different controller settings. The measurement equipment 10 then makes three measurements through the main calibration path 42 with the main path polarization controller 20 operatively coupled to generate three matrices $M_3$, $M_4$, and $M_5$ as follows:

$$\overline{M}_3 = \overline{B}\overline{K}\overline{R}_4\overline{J}\overline{A} \qquad (23)$$

$$\overline{M}_4 = \overline{B}\overline{V}\overline{R}_5\overline{J}\overline{A} \qquad (24)$$

$$\overline{M}_5 = \overline{B}\overline{V}\overline{R}_6\overline{J}\overline{A} \qquad (25)$$

The three matrices $M_3$, $M_4$, and $M_5$ contain information about the Source Connector error, $\overline{J}$, and the Detector Connector error, $\overline{K}$, and can therefore be used to correct for these errors. As a first step in the process of finding these matrices that correct for the Source Connector $\overline{J}$ and the Detector Connector error, $\overline{K}$, the three matrices $M_3$, $M_4$, and $M_5$ are corrected using the source, $\overline{S}'$, and detector, $\overline{D}'$, correction matrices determined from the re-calibration path 40:

$$\overline{M}_3^c = (\overline{R}_{VB}\overline{V}^{-1}\overline{B}^{-1})(\overline{B}\overline{K}\overline{R}_4\overline{J}\overline{A})(\overline{A}^{-1}\overline{Q}^{-1}\overline{R}_{AQ}) = \overline{R}_{VB}\overline{V}^{-1}\overline{K}\overline{R}_4 \overline{J}\overline{Q}^{-1}\overline{R}_{AQ} \qquad (26)$$

$$\overline{M}_4^c = (\overline{R}_{VB}\overline{V}^{-1}\overline{B}^{-1})(\overline{B}\overline{K}\overline{R}_5\overline{J}\overline{A})(\overline{A}^{-1}\overline{Q}^{-1}\overline{R}_{AQ}) = \overline{R}_{VB}\overline{V}^{-1}\overline{K}\overline{R}_5 \overline{J}\overline{Q}^{-1}\overline{R}_{AQ} \qquad (27)$$

$$\overline{M}_5^c = (\overline{R}_{VB}\overline{V}^{-1}\overline{B}^{-1})(\overline{B}\overline{K}\overline{R}_6\overline{J}\overline{A})(\overline{A}^{-1}\overline{Q}^{-1}\overline{R}_{AQ}) = \overline{R}_{VB}\overline{V}^{-1}\overline{K}\overline{R}_6 \overline{J}\overline{Q}^{-1}\overline{R}_{AQ} \qquad (28)$$

The main calibration path matrices are then calculated using the Basic Calibration Algorithms to give:

$$BCA_S(\overline{M}_4^c, \overline{M}_5^c, \overline{M}_6^c) = BCA_S(\overline{R}_{VB}\overline{V}^{-1}\overline{K}\overline{R}_4\overline{J}\overline{Q}^{-1}\overline{R}_{AQ}, \overline{R}_{VB}\overline{V}^{-1}\overline{K}\overline{R}_5\overline{J}\overline{Q}^{-1}\overline{R}_{AQ}, \overline{R}_{VB}\overline{V}^{-1}\overline{K}\overline{R}_6\overline{J}\overline{Q}^{-1}\overline{R}_{AQ}) = \overline{S}'' = \overline{R}_{AQ}^{-1}\overline{Q}\overline{J}^{-1}\overline{R}_{QJ} \qquad (29)$$

and $$BCA_D(\overline{M}_4^c, \overline{M}_5^c, \overline{M}_6^c) = BCA_D(\overline{R}_{VB}\overline{V}^{-1}\overline{K}\overline{R}_4\overline{J}\overline{Q}^{-1}\overline{R}_{AQ}, \overline{R}_{VB}\overline{V}^{-1}\overline{K}\overline{R}_5\overline{J}\overline{Q}^{-1}\overline{R}_{AQ}, \overline{R}_{VB}\overline{V}^{-1}\overline{K}\overline{R}_6\overline{J}\overline{Q}^{-1}\overline{R}_{AQ}) = \overline{D}'' = \overline{R}_{KV}\overline{K}^{-1}\overline{V}\overline{R}_{VB}^{-1} \qquad (30)$$

These matrices do not contain information about the large sources of error corresponding to the source and detector optics in the measurement equipment, $\overline{A}$ and $\overline{B}$, and only contain information about the smaller and more stable errors induced by the Source Connector 22, $\overline{J}$, the Detector Connector, $\overline{K}$, and the switches 30 and 34, $\overline{Q}$ and $\overline{V}$. These matrices, $\overline{D}''$, and $\overline{S}''$ should then remain stable over long periods of time.

We can now calculate a total source correction matrix, $\overline{S}'''$, where:

$$\overline{S}''' = \overline{S}'\overline{S}'' = (\overline{A}^{-1}\overline{Q}^{-1}\overline{R}_{AQ})(\overline{R}_{AQ}^{-1}\overline{Q}\overline{J}^{-1}\overline{R}_{QJ}) = \overline{A}^{-1}\overline{J}^{-1}\overline{R}_{QJ}. \qquad (31)$$

We can also calculate a total detector correction matrix, $\overline{D}'''$, where:

$$\overline{D}''' = \overline{D}'\overline{D}'' = (\overline{R}_{KV}\overline{K}^{-1}\overline{V}\overline{R}_{VB}^{-1})(\overline{R}_{VB}\overline{V}^{-1}\overline{B}^{-1}) = \overline{R}_{KV}\overline{K}^{-1}\overline{B}^{-1}. \qquad (32)$$

Subsequent DUT measurements are then calculated and corrected using these total correction matrices, which correct for the internal source optics 28, $\overline{A}$, the internal detector optics 36, $\overline{B}$, the source connector 22, $\overline{J}$, and the detector connector 24, $\overline{K}$. These total source, $\overline{S}'''$, and total detector, $\overline{D}'''$ correction matrices are the matrices that we set out to find in paragraph 44.

Now, if an imperfect instrument is used to measure a device with a transfer matrix, $\overline{X}$, a matrix will be measured which includes the effects of the internal source optics 28, $\overline{A}$, the internal detector optics 36, $\overline{B}$, the source connector 22, $\overline{J}$ and the detector connector 24, $\overline{K}$.

$$\overline{M}_{ex} = \overline{B}\overline{K}\overline{X}\overline{J}\overline{A} \qquad (33)$$

Applying the total source, $\overline{S}'''$, and total detector, $\overline{D}'''$ correction matrices, however, allows removal of the effects of the internal source optics 28, $\overline{A}$, the internal detector optics 36, $\overline{B}$, the source connector 22, $\overline{J}$, and the detector connector 24, $\overline{K}$, from the measurement, while introducing only two arbitrary rotation matrices, $\overline{R}_{KV}$, and $\overline{R}_{QJ}$:

$$\overline{M}_{ex}^c = \overline{D}'''\overline{M}_{ex}\overline{S}''' = (\overline{R}_{KV}\overline{K}^{-1}\overline{B}^{-1})(\overline{B}\overline{K}\overline{X}\overline{J}\overline{A})(\overline{A}^{-1}\overline{J}^{-1}\overline{R}_{QJ}) = \overline{R}_{KV}\overline{X}\overline{R}_{QJ} \qquad (34)$$

If the internal source optics 28 and/or the internal detector optics 34 drift so that the matrices representing them change from $\overline{A}$ and $\overline{B}$ to $\overline{A}_{drift}$ and $\overline{B}_{drift}$, then we repeat the three measurements through the re-calibration device. This is done without disturbing the DUT, $\overline{X}$, connected to the source connector 22 and the detector connector 24. We then get a new set of measurements through the re-calibration device:

$$\overline{M}_0^{drift} = \overline{B}_{drift}\overline{V}\overline{R}_0\overline{Q}\overline{A}_{drift} \qquad (35)$$

$$\overline{M}_1^{drift} = \overline{B}_{drift}\overline{V}\overline{R}_1\overline{Q}\overline{A}_{drift} \qquad (36)$$

$$\overline{M}_2^{drift} = \overline{B}_{drift}\overline{V}\overline{R}_2\overline{Q}\overline{A}_{drift} \qquad (37)$$

And we calculate a new set of calibration matrices, $\overline{S}_{drift}'$ and $\overline{D}_{drift}'$, $$BCA_S(\overline{M}_0^{drift}, \overline{M}_1^{drift}, \overline{M}_2^{drift}) = BCA_S(\overline{B}_{drift}\overline{V}\overline{R}_0\overline{Q}\overline{A}_{drift}, \overline{B}_{drift}\overline{V}\overline{R}_0\overline{Q}\overline{A}_{drift}, \overline{B}_{drift}\overline{V}\overline{R}_0\overline{Q}\overline{A}_{drift}) = \overline{S}_{drift}' = \overline{A}_{drift}^{-1}\overline{Q}^{-1}\overline{R}_{AQ} \qquad (38)$$

and $$BCA_D(\overline{M}_0^{drift}, \overline{M}_1^{drift}, \overline{M}_2^{drift}) = BCA_D(\overline{B}_{drift}\overline{V}\overline{R}_0\overline{Q}\overline{A}_{drift}, \overline{B}_{drift}\overline{V}\overline{R}_0\overline{Q}\overline{A}_{drift}, \overline{B}_{drift}\overline{V}\overline{R}_0\overline{Q}\overline{A}_{drift}) = \overline{D}_{drift}' = \overline{R}_{VB}\overline{V}^{-1}\overline{B}_{drift}^{-1} \qquad (39)$$

If the three rotation states, $\overline{R}_0$, $\overline{R}_1$, and $\overline{R}_2$ of the re-calibration device are the same as in the original calibration, (e.g., the fiber-loop paddles are rotated to the same angles), then the rotation matrices, $\overline{R}_{AQ}$ and $\overline{R}_{VB}$, included in the correction matrices, $\overline{D}'_{drift}$ and $\overline{S}'_{drift}$ will be identical to those calculated in the original calibration. Achieving identical rotation states on the re-calibration is therefore an important, but not necessarily difficult to achieve with mechanized control of the re-calibration device.

With this re-calibration completed, we compute a new set of total correction matrices using our new $\overline{D}'_{drift}$ and $\overline{S}'_{drift}$, and our old $\overline{D}''$ and $\overline{S}''$:

$$\overline{S}'''_{drift} = \overline{S}'_{drift}\overline{S}'' = (\overline{A}_{drift}^{-1}\overline{Q}^{-1}\overline{R}_{AQ})(\overline{R}_{AQ}^{-1}\overline{Q}\overline{J}^{-1}\overline{R}_{QJ}) = \overline{A}_{drift}^{-1}\overline{J}^{-1}\overline{R}_{QJ} \qquad (40)$$

and $$\overline{D}'''_{drift} = \overline{D}''\overline{D}'_{drift} = (\overline{R}_{KV}\overline{K}^{-1}\overline{V}\overline{R}_{VB}^{-1})(\overline{R}_{VB}\overline{V}^{-1}\overline{B}_{drift}^{-1}) = \overline{R}_{KV}\overline{K}^{-1}\overline{B}_{drift}^{-1} \qquad (41)$$

So, if we make a measurement through the DUT after some drift has occurred, we will get:

$$\overline{M}_{ex} = \overline{B}_{drift} \overline{KXJA}_{drift} \quad (42)$$

By applying the new total calibration matrices generated through the re-calibration path without the need to disconnect or disturb the DUT, the following is produced:

$$\overline{M}_{ex}{}^c = \overline{D}'''_{drift} \overline{M}_{ex} \overline{S}'''_{drift} = (\overline{R}_{KV}\overline{K}^{-1}\overline{B}_{drift}{}^{-1})(\overline{B}_{drift} \overline{KXJA}_{drift})(\overline{A}_{drift}{}^{-1}\overline{J}^{-1}\overline{R}_{QJ}) = \overline{R}_{KV}\overline{XR}_{QJ} \quad (43)$$

which is then the correct measurement of the DUT, and even has the same rotation matrices, $\overline{R}_{KV}$ and $\overline{R}_{QJ}$, as the measurement taken prior to the drift of the internal source optics 28 and/or the internal detector optics 36.

This analytically demonstrated ability to recover from a change in the internal source optics 28 and/or the internal detector optics 36 is an important aspect and benefit of this invention. Although the above description involves substantial number of matrices used in the model, most are never directly calculated. To emphasize this point, the calibration process is now summarized without including calculation not needed the actual implementation of the calibration process.

Step 1. Measure three matrices through the re-calibration device 32 at three different rotation settings: $\overline{M}_0$, $\overline{M}_1$, and $\overline{M}_2$. Calculate a set of source $\overline{S}'$ and detector $\overline{D}'$ matrices from these three measurements using the Basic Calibration Algorithm, $$BCA_S(\overline{M}_0, \overline{M}_1, \overline{M}_2) = \overline{S}' \quad (44)$$

and $$BCA_D(\overline{M}_0, \overline{M}_1, \overline{M}_2) = \overline{D}' \quad (45)$$

Step 2. Measure three matrices through the main calibration path at three different rotation settings of the calibration device 20, $\overline{M}_3$, $\overline{M}_4$, and $\overline{M}_5$. These measurements are corrected using $\overline{S}'$ and $\overline{D}'$, to produce $\overline{M}_3{}^c$, $\overline{M}_4{}^c$, and $\overline{M}_5{}^c$, as shown below:

$$\overline{M}_3{}^c = \overline{D}' \overline{M}_3 \overline{S}' \quad (46)$$

$$\overline{M}_4{}^c = \overline{D}' \overline{M}_4 \overline{S}' \quad (47)$$

$$\overline{M}_5{}^c = \overline{D}' \overline{M}_5 \overline{S}' \quad (48)$$

Calculate a set of source $\overline{S}''$ and detector $\overline{D}''$ matrices from these three measurements using the Basic Calibration Algorithm:

$$BCA_S(\overline{M}_3{}^c, \overline{M}_4{}^c, \overline{M}_5{}^c) = \overline{S}'' \quad (49)$$

and $$BCA_D(\overline{M}_3{}^c, \overline{M}_4{}^c, \overline{M}_5{}^c) = \overline{D}'' \quad (50)$$

Step 3. Calculate a set of total correction matrices:

$$\overline{S}''' = \overline{S}' \overline{S}'' \quad (51)$$

and $$\overline{D}''' = \overline{D}'' \overline{S}' \quad (52)$$

Step 4. If the internal source optics 28 or internal detector optics 24 drift, repeat step 1 and step 3 using the stored matrices $\overline{S}''$ and $\overline{D}''$.

Figure 10:
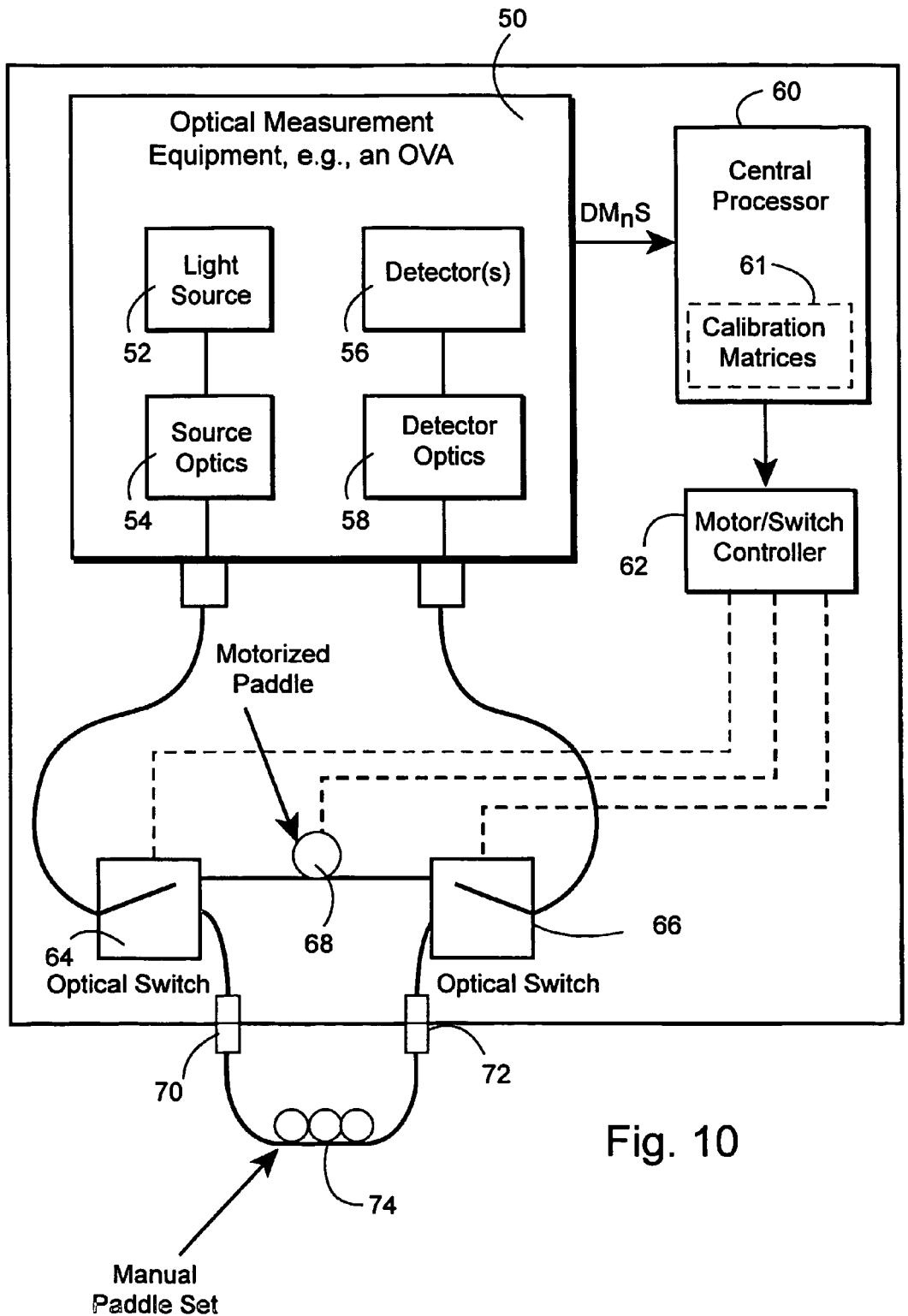
FIG. 10 illustrates one non-limiting, example implementation in which a lossless fiber loop is coupled to the source and detector connectors of the main calibration paths.

The dual calibration described above was tested by constructing a calibration network similar to that represented in FIG. 10 using an OVA 50 of current production design. However, the invention is in no way limited to this test system implementation. The OVA 50 includes a light source 52, e.g., a laser, coupled to source optics 54, which are coupled to a source connector. The detector optics 58 are connected to the detector connector and one or more detectors 56, e.g., photodiodes. A first optical switch 64 is coupled to the source connector and can be, for example, a Grumman MEMs switch. A second optical switch 66 is coupled to the detector connector and can be, for example, a Lighttech switch. The positions of the first and second switches 64 and 66 are controlled by a signal generated by the motor/switch controller 62, which itself is controlled by a central processor 60 that stores various calibration matrices 61 calculated using the equations described above. A main path calibration polarization controller 68 may be, for example, a motorized, quarter wavelength fiber loop paddle, the positions of which are controlled by a signal generated by the motor/switch controller 62. The entire calibration network was assembled, just for test purposes, on a motor-optics circuit board. Other configurations and implementations may be employed.

For the main path calibration, the three main calibration measurement matrices $M_0$-$M_2$ must be taken at the same three paddle positions each time the OVA 50 is re-calibrated. The OVA 50 generates measurement data represented as $DM_nS$ and provides it to the central processor 60. That data includes the main path measurement data $M_0$-$M_2$ and the detector and source error matrices D and S. The main path calibration matrices $\overline{S}''$ and $\overline{D}''$ generated as a result of the main path calibration procedures are stored by the central processor 60 in memory 61.

Figure 11:
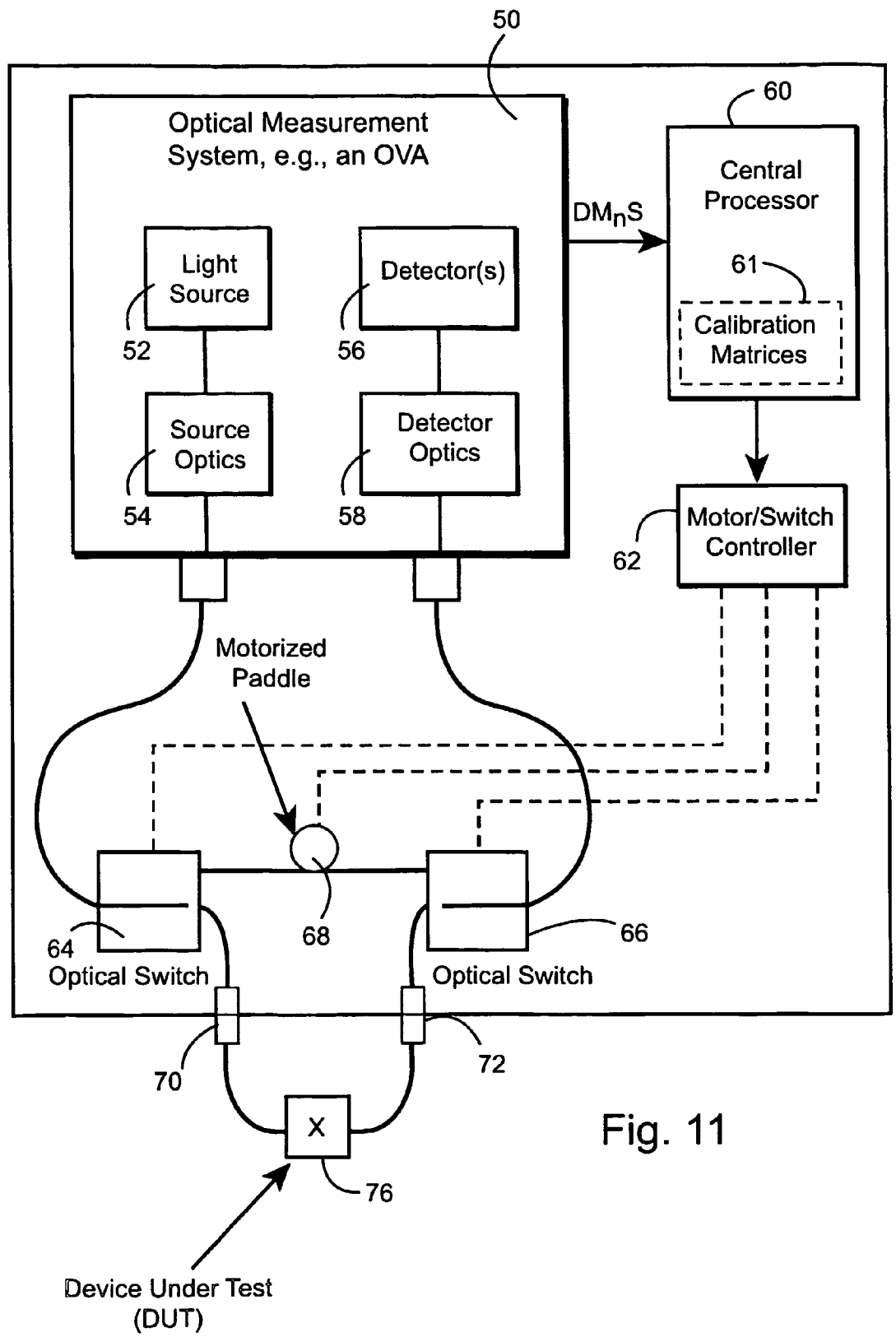
FIG. 11 illustrates that same system as FIG. 10 but with the device under test connected between the source and detector connectors.

FIG. 11 shows the same network, after the initial main path calibration, testing a DUT 76, represented as matrix X. Now the OVA 50 produces a measurement output corresponding to DXS, where D and S are the detector and source error matrices. Before beginning the main path calibration, the motorized paddle of the polarization controller 74 was moved to a counter-clockwise stop corresponding to 0°. When prompted for the first paddle movement, the paddle was commanded to move 116 steps clockwise, which corresponds to slightly more than 45° of rotation. At the second prompt to move the paddles, the motorized paddle was moved another 116 steps clockwise corresponding to 90°. The paddle remained in this 90° position for all subsequent measurements.

During DUT testing after the main path calibration, the re-calibration operation described above was carried out periodically, but it can be done whenever desired. Each re-calibration operation produces updated source and detector error correction matrices. The central processor 60 applies the re-calibration source and detector error correction matrices to the output of the OVA 50 to generate a matrix measurement of the DUT that is accurate and not biased by affects of the source and detector optics—even if the source and detector-optic characteristics may change over time and/or temperature.

The OVA 50 was run during the testing using standard software, e.g., OVA_Main v 3.0. This software stores the calibration matrices $\overline{S}$ and $\overline{D}$ in files 61 that are loaded when the OVA 50 is started up. By re-starting the software, the calibration matrices can be re-loaded into RAM from files on the computer hard-drive. This facilitated re-calibrating source and detector error matrices since the OVA already performed the Basic Calibration Algorithm and stored the results into files. Testing the concept required only that the files be manipulated to carry out the matrix multiplications described above in Step 3, and the replacement of the OVA software calibration files with the new total calibration files.

As described earlier, the calibration files for the source and detector connectors were generated during the initial, main path calibration by taking three measurements through the manual paddle set 74 at the standard three paddle positions. The three resulting files were saved as source and detector connector matrix files over the same wavelength range as the main path calibration files. A program was then run that read in these three files along with the source and detector error calibration matrices, and calculated a new set of calibration matrices from this information following step 3 above. The calibration file was then replaced with this new set of calibration matrices that accounted for errors in the source connector 22 and the detector connector 24.

Figure 12A:
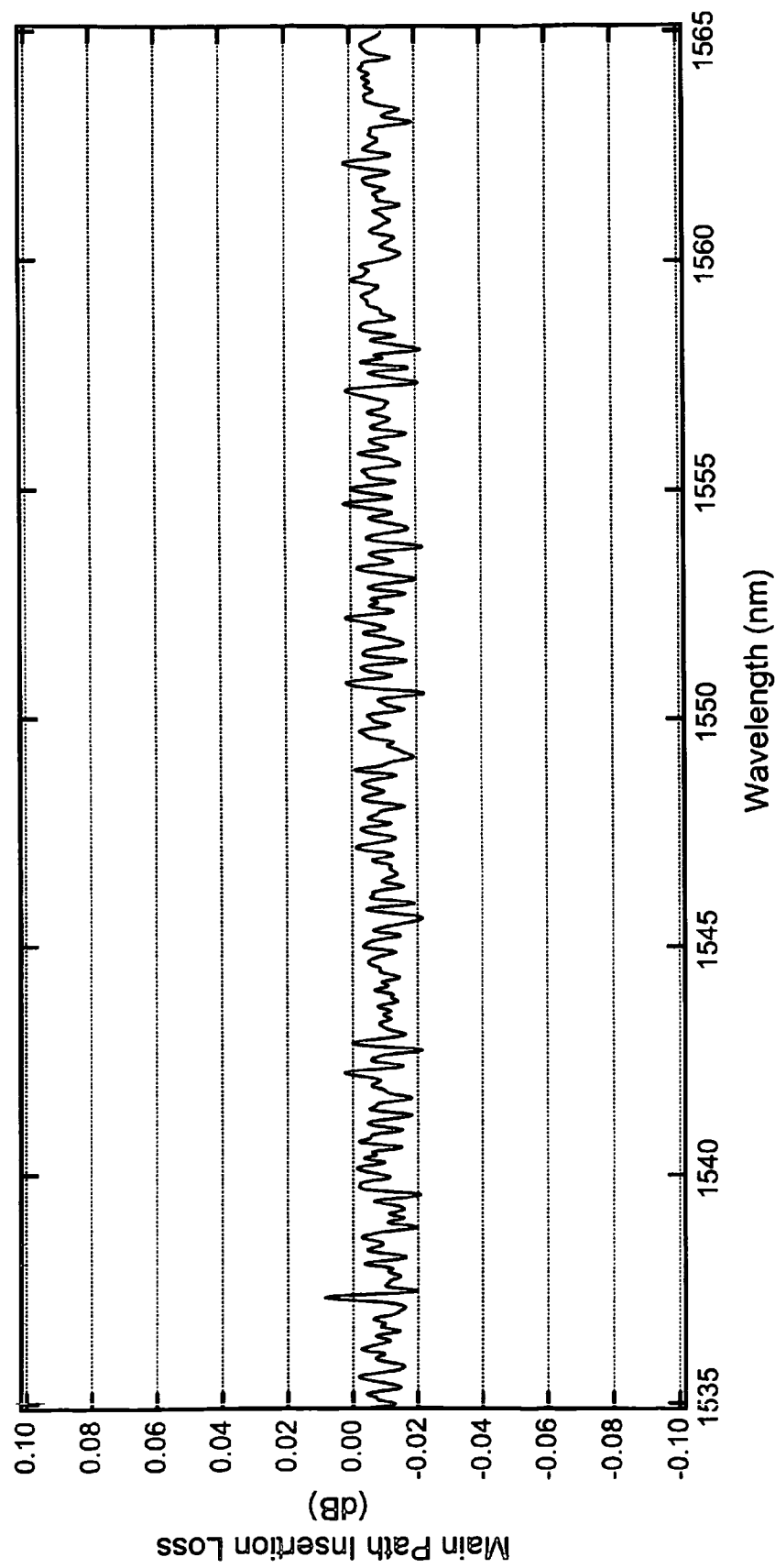
FIGS. 12A and 12B illustrate main path insertion loss and PDL as a function of wavelength for a calibrated measurement device.
Figure 12B:
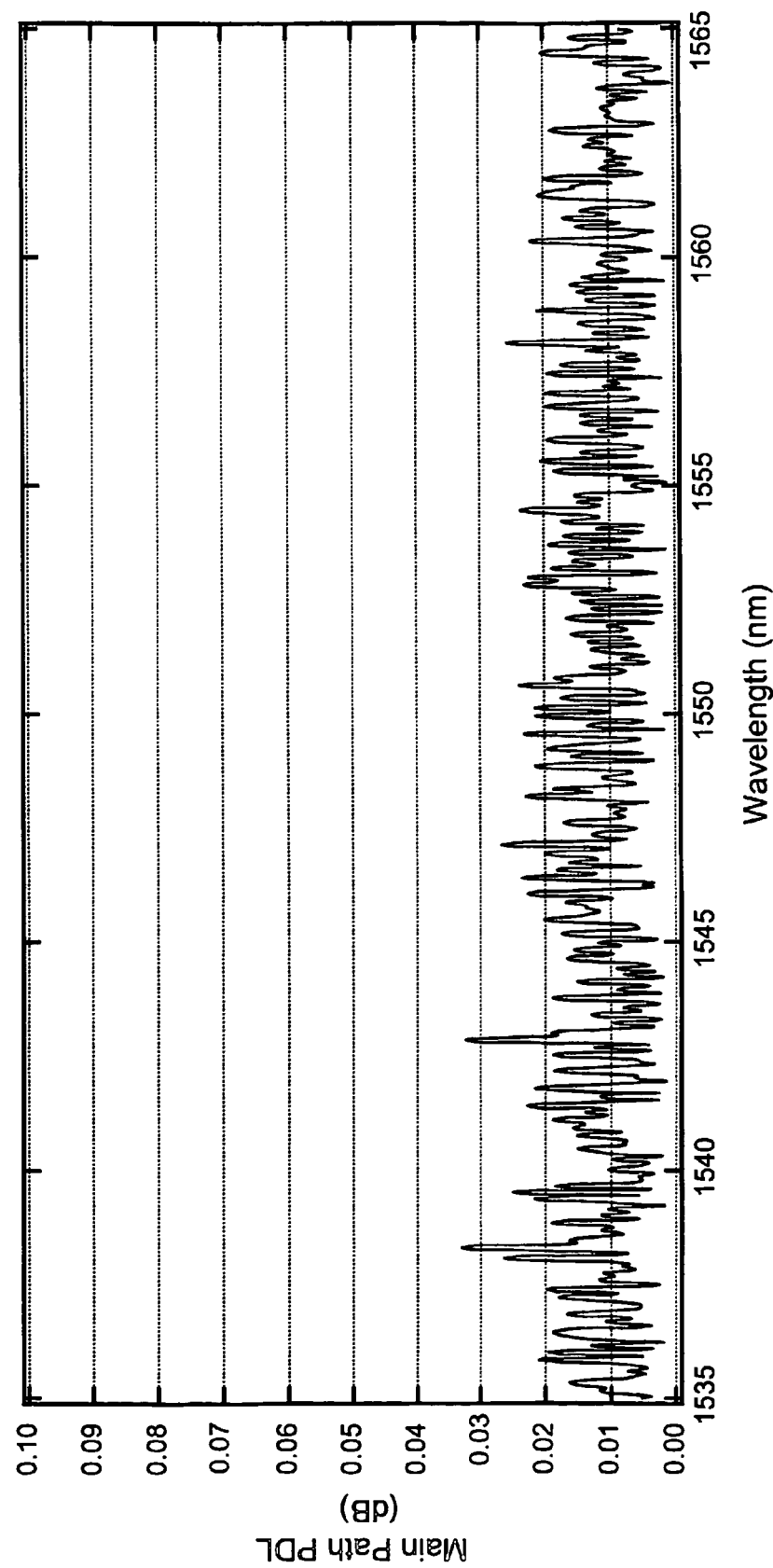

The OVA software was then loaded with this new calibration data, and when a measurement through the manual paddle set 74 coupled to the main path was taken, insertion loss versus wavelength and PDL versus wavelength data through the main calibration path below was obtained. Those data are plotted in graphical form in FIGS. 12A and 12B. The insertion loss is near zero dB and the PDL is also very low indicating that the OVA 50 is well-calibrated.

Figure 13A:
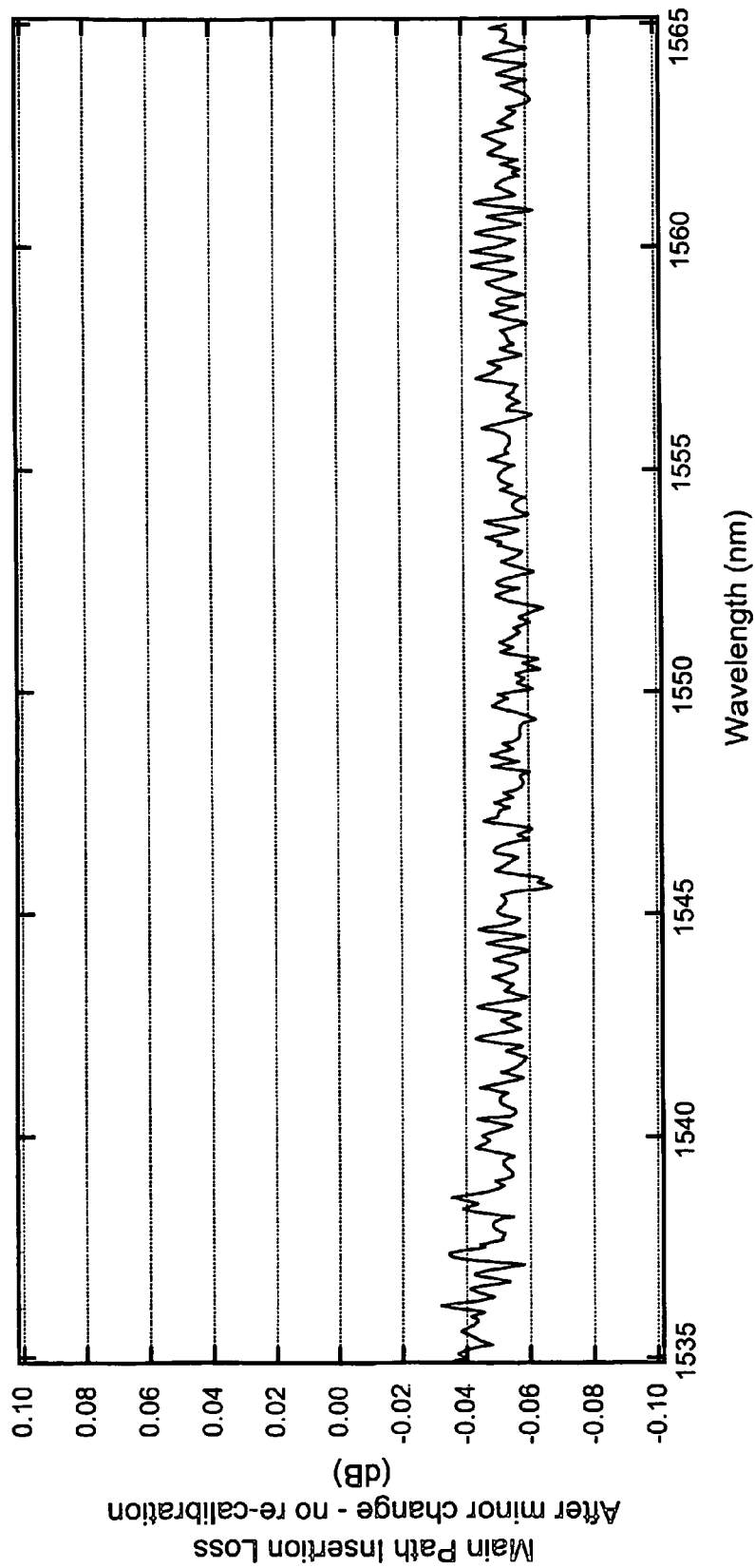
FIGS. 13A and 13B main path insertion loss and PDL after a minor change in the thermal optics.
Figure 13B:
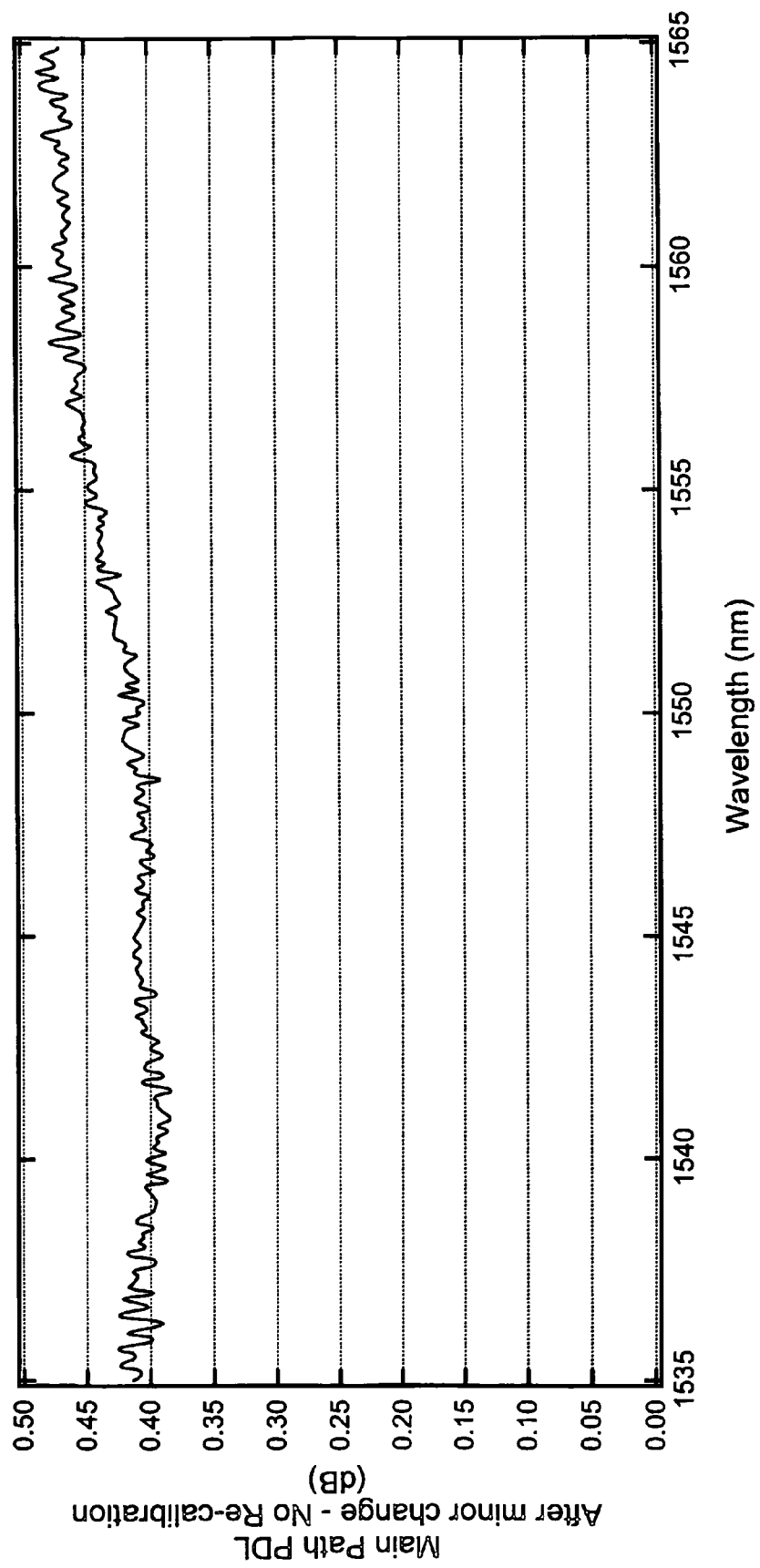

Next, the internal source and detector optics of the OVA 50 were purposefully disturbed using minor movements of the internal source optics. This effectively changes the optical network, and the error matrix, $\bar{A}$, and simulates drift in the optical network. The main calibration path was then re-measured, and the results obtained are illustrated in FIGS. 13A and 13B. Although, the changes to the insertion loss measurement are relatively small, the changes to the PDL are substantial. This is typical of the sort of error that would be caused by a change in temperature of 3° or 4° C. In any event, the change resulted in the OVA 50 no longer being well-calibrated.

Figure 14A:
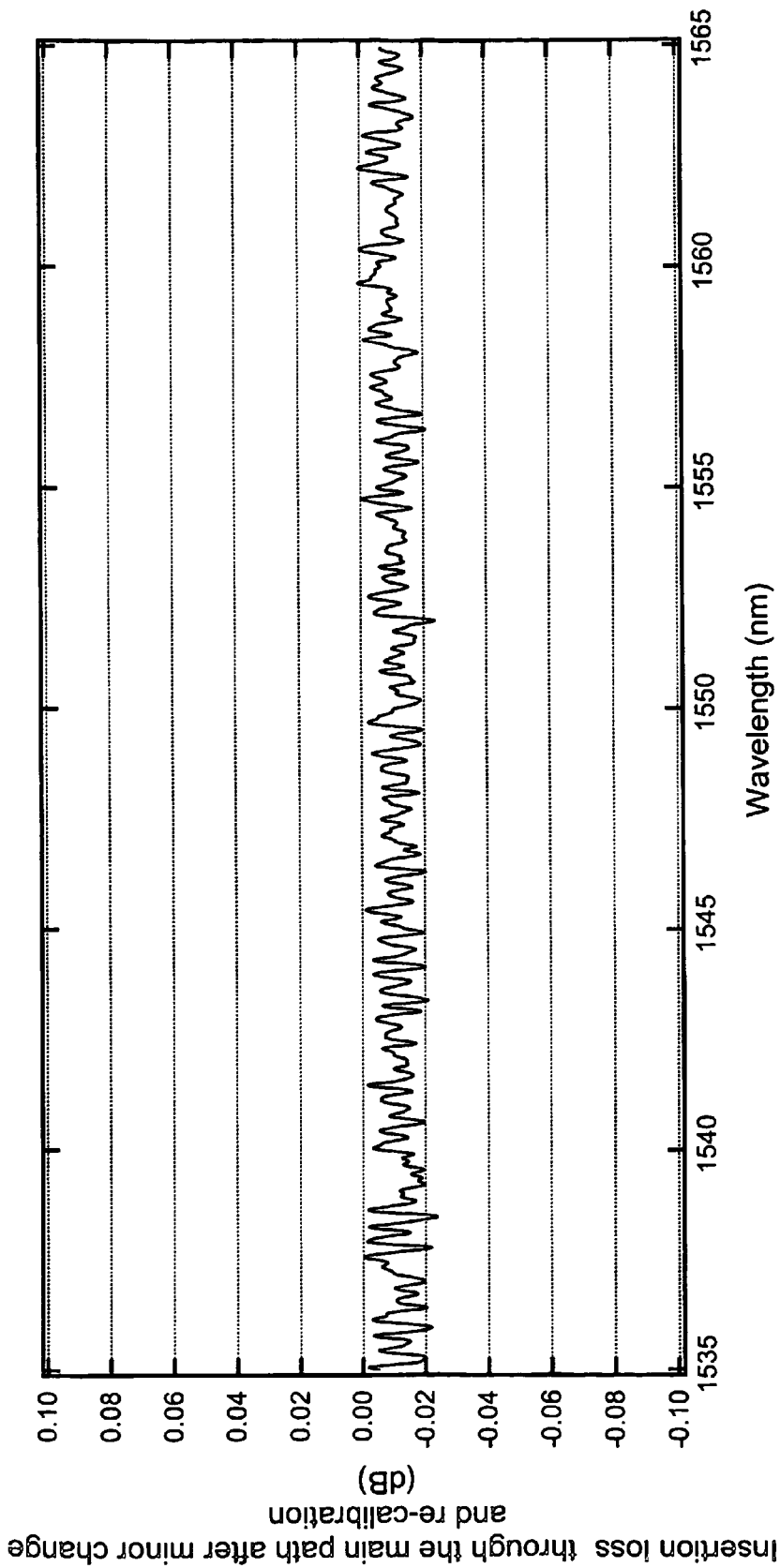
FIGS. 14A and 14B illustrate main path insertion loss and PDL after a minor change in the optical component followed by a re-calibration.
Figure 14B:
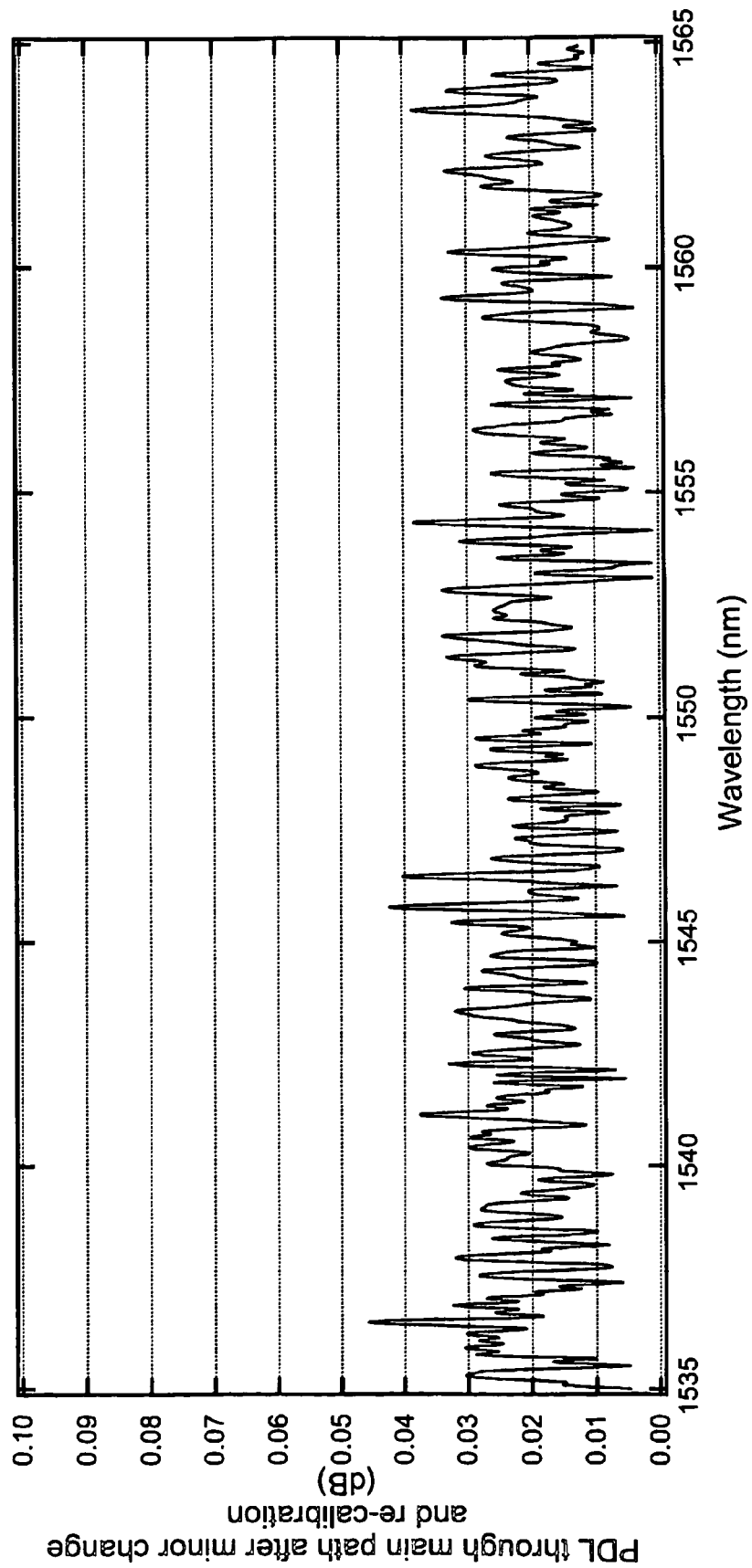

The optical switches 64 and 66 were then configured for a re-calibration operation, and the re-calibration motorized paddle 68 moved to the ccw stop, 0°. The measurement sequence was run again, and the re-calibration matrices were calculated. Note that the paddles, which are switched in for the DUT, were never disconnected, and did not need to be moved, thus achieving the goal of re-calibrating without the need to disturb the DUT. The OVA software was then restarted using the new calibration files, and the switches 64 and 66 configured to measure through the main path. The data illustrated in FIGS. 14A and 14B show that the re-calibration worked brought the insertion loss near zero and much reduced the PDL.

Figure 15A:
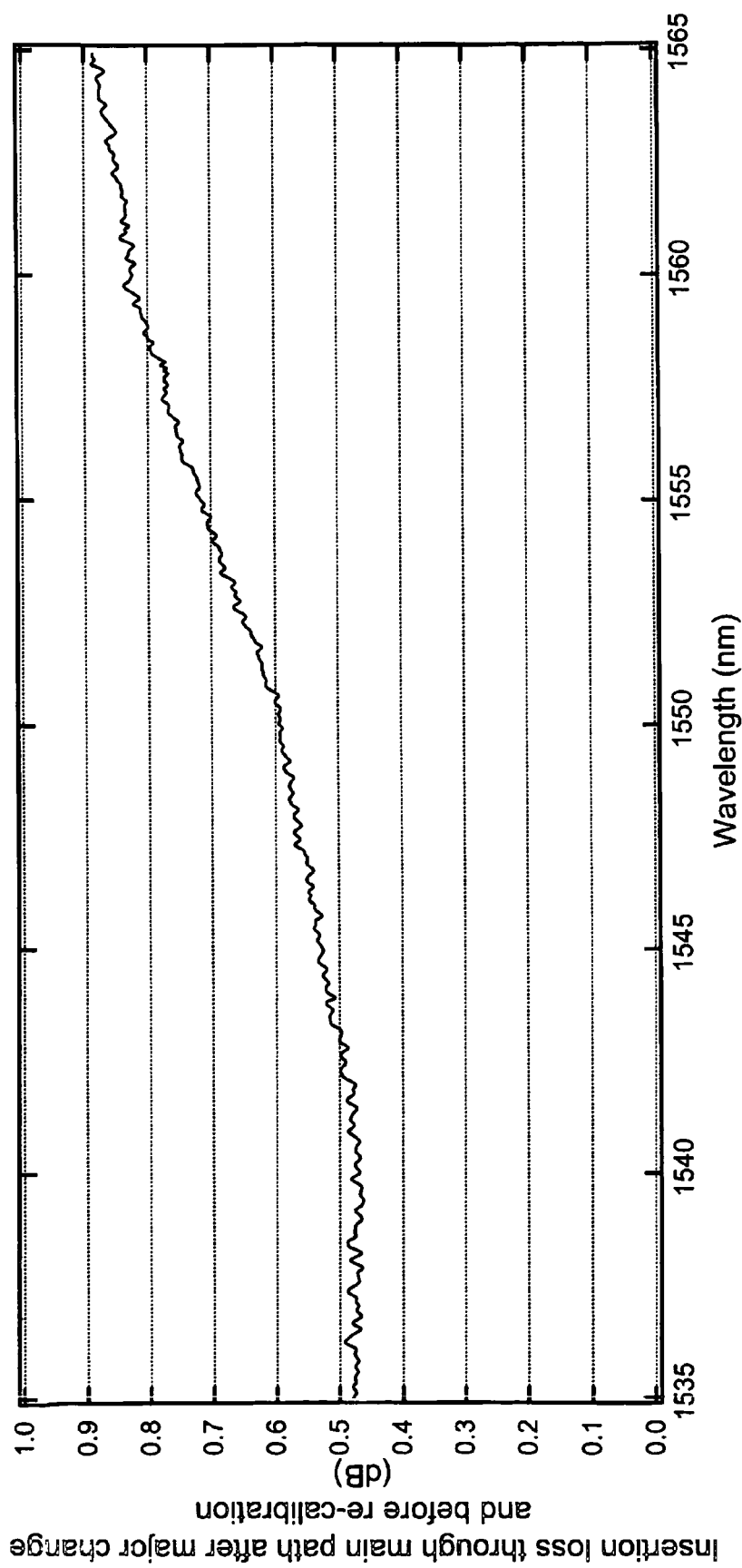
FIGS. 15A and 15B illustrate main path insertion loss and PDL after a major change in the optical components before re-calibration.
Figure 15B:
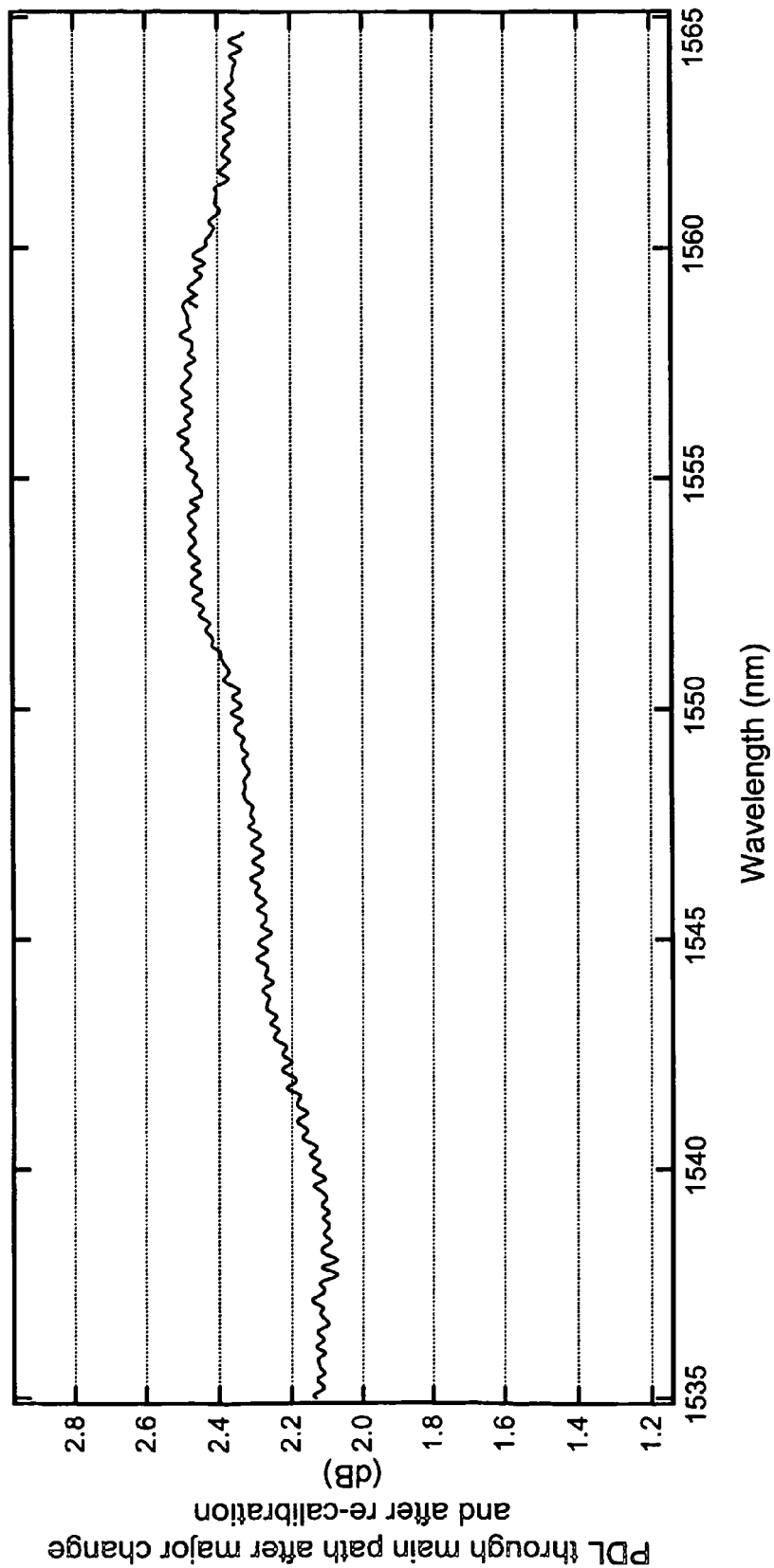

Next, a major disturbance to the internal source optics was intentionally carried out. The main calibration path was measured again and produced the results shown in FIGS. 15A and 15B. This level of error is the sort that may occur with no calibration at all, and it exceeds what normally occurs with typical "drift."

Figure 16A:
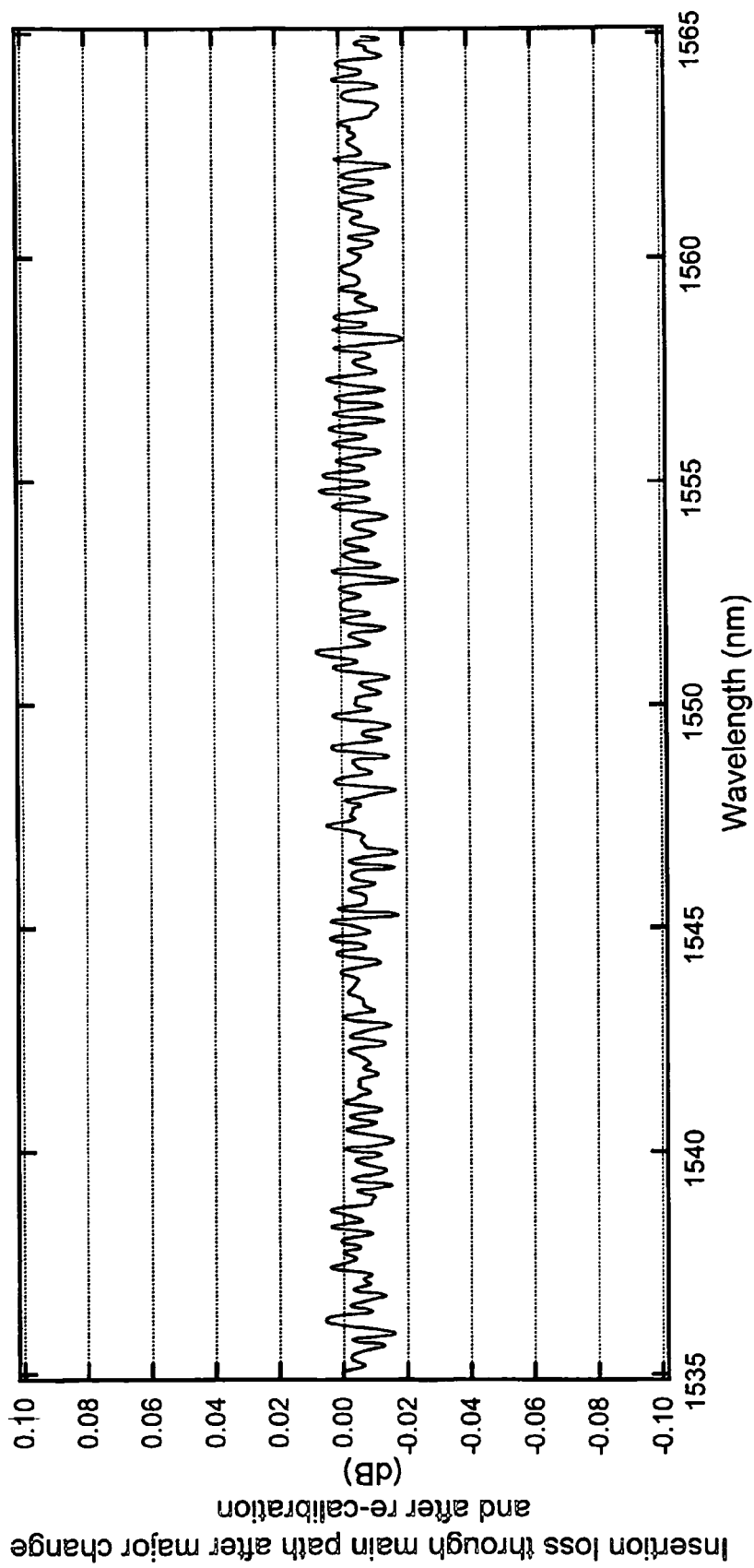
FIGS. 16A and 16B illustrate main path insertion loss and PDL after a major change in the optical components and after re-calibration.
Figure 16B:
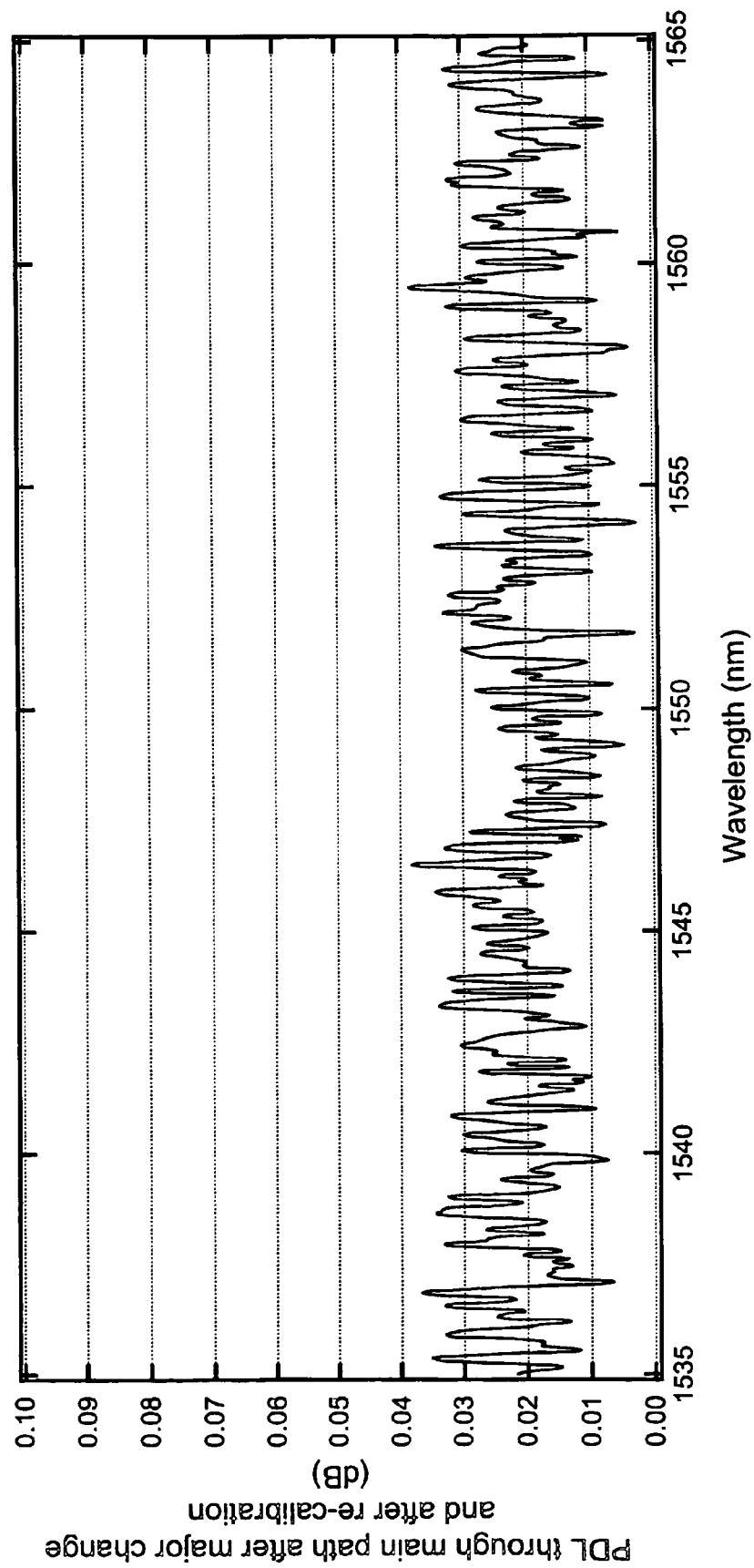

A re-calibration was performed, and the main calibration path re-measured, resulting in the data shown in FIGS. 16A and 16B. Again, the insertion loss is returned to near zero, and the PDL was reduced considerably. As the test data show, the re-calibration operations carried out using the re-calibration path corrected for small and large changes in the internal OVA optics, demonstrating both accuracy and robustness.

To simplify the description up to this point, the measurement equipment was assumed to be measuring a single input port—single output port DUT. But in practice this assumption may not be true. Adding a 1×N switch to the source port and 1×M switch to the detector port of the measurement equipment provides multi-port/multi-channel capability. But such switches may produce significant (e.g., 0.07 dB) PDL, and thus, those switches should be properly accounted for in the calibration.

The single re-calibration path approach can be expanded to calibrate multi-port/multi-channel DUTs to maintain calibration over long periods of time. But at first glance, this "expansion" appears to be a daunting problem. A 2×2 switch matrix contains four potential paths, which may be manageable. A 40×40 switch matrix will contain 1600 potential paths, which is much less manageable. Recalibrating 40-port DUT would take excessive amounts of time and/or processing resources to be acceptable, particularly if the re-calibration is performed frequently. How this problem is overcome is now described.

Figure 17:
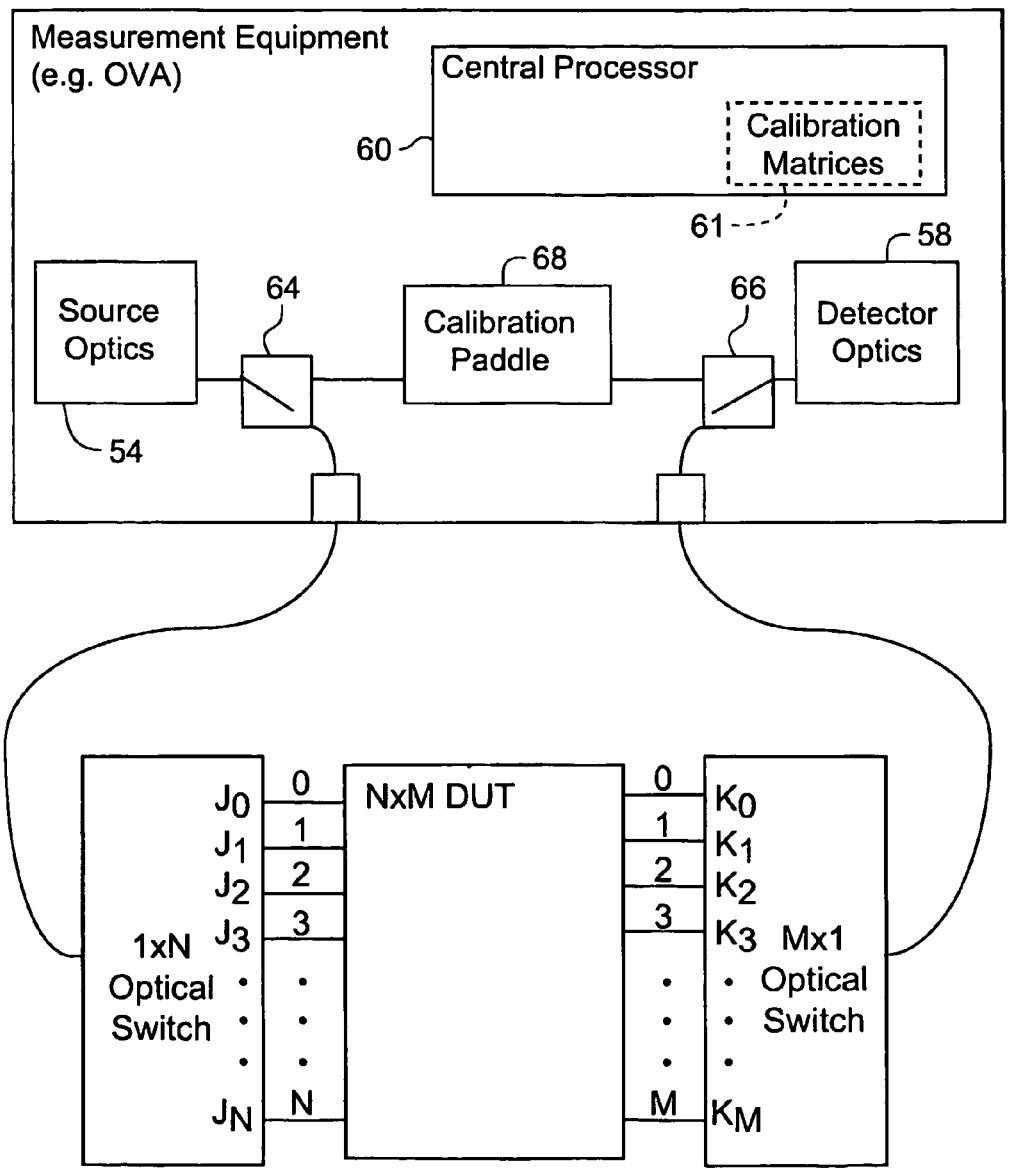
FIG. 17 illustrates a multi-channel measurement system constructed by connecting 1×N and 1×M switches to an optical measurement system.
Figure 18:
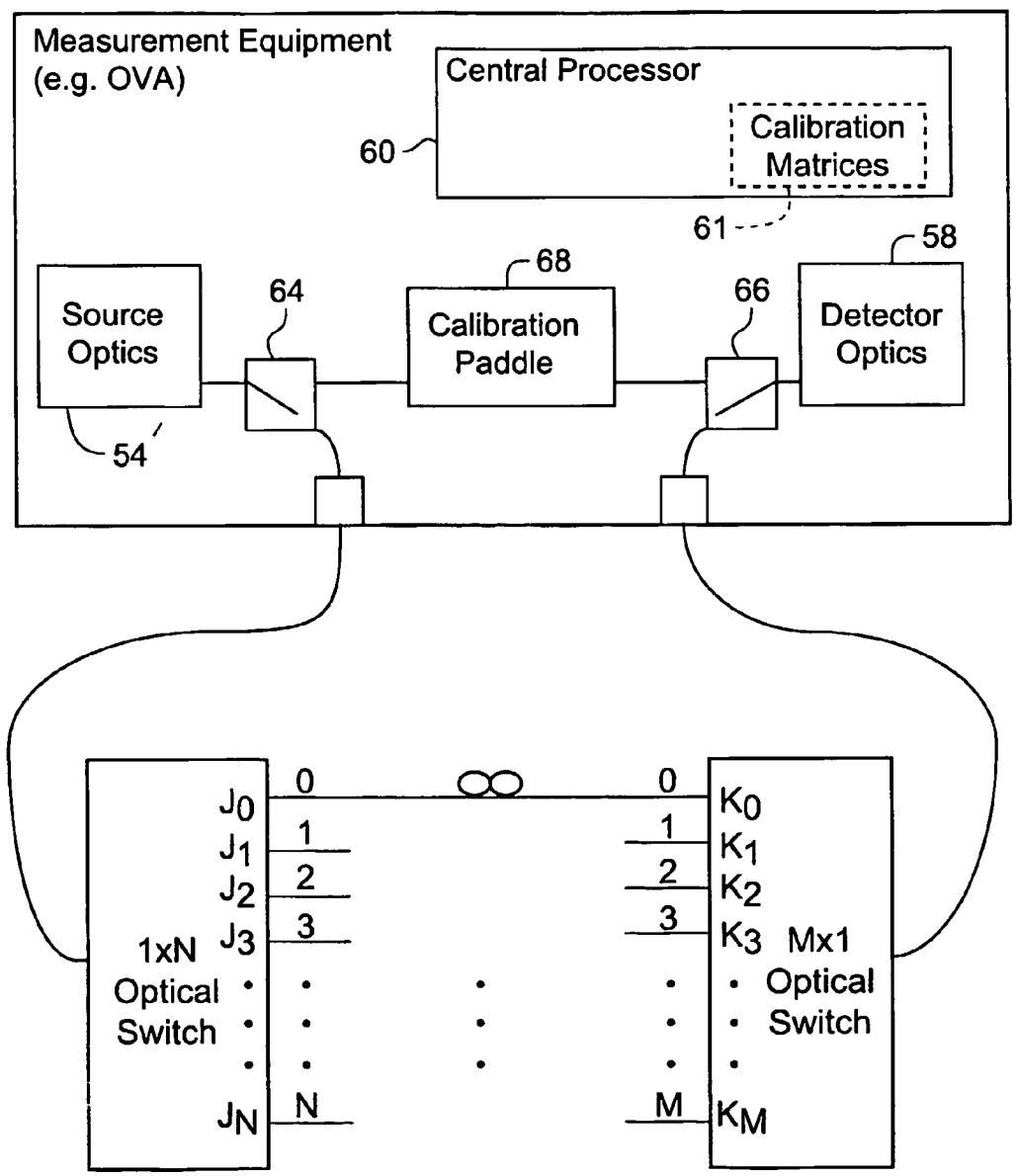
FIG. 18 illustrates a multi-channel measurement system constructed by connecting the 1×N and 1×M switches to an optical measurement system with a calibration device connected between source port 0 and detector port 0 for the first step in the calibration.
Figure 19:
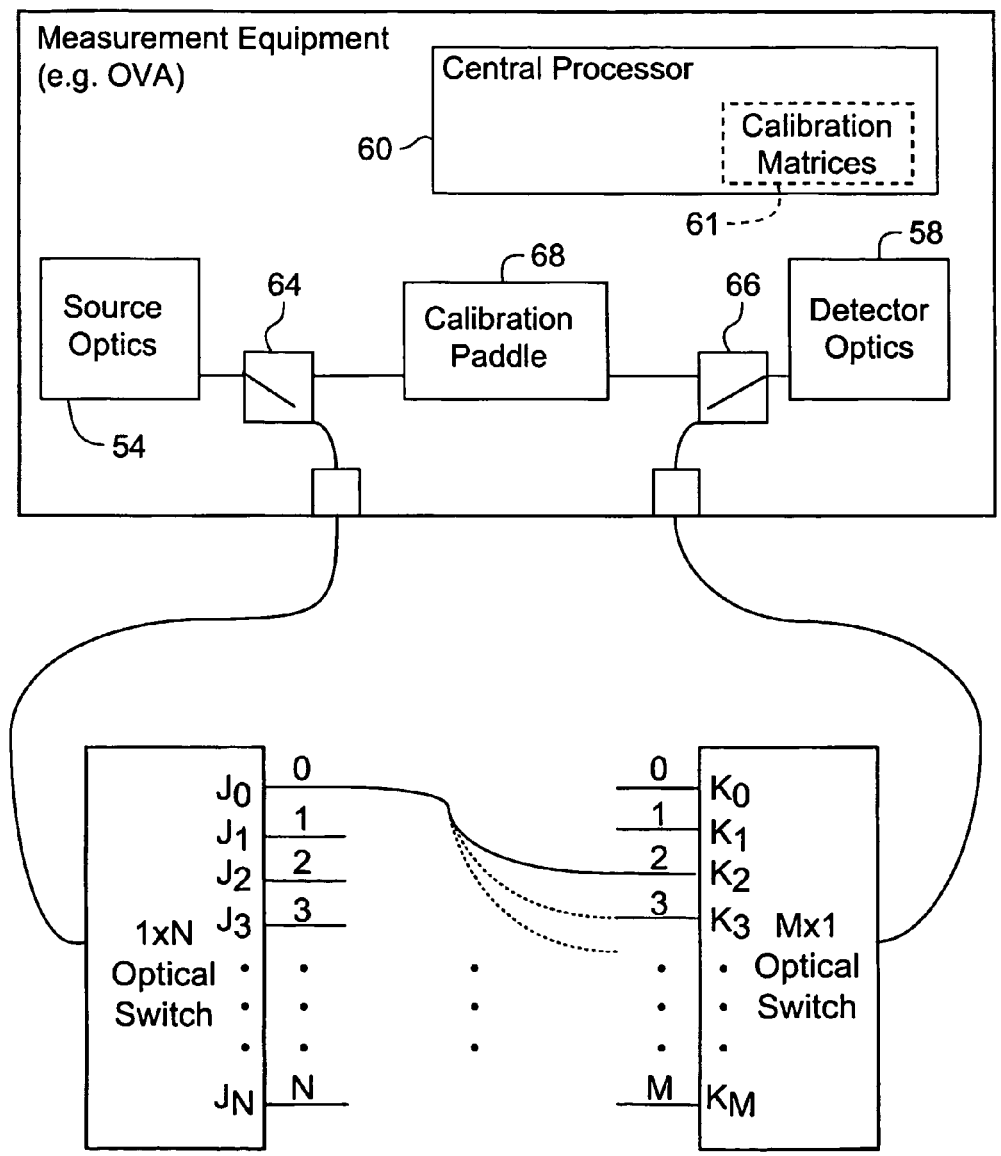
FIG. 19 illustrates a multi-channel measurement system constructed by connecting the 1×N and 1×M switches to an optical measurement system with a calibration device connected between source port 0 and detector port m for the second step in the calibration.

FIG. 17 shows how a general N×M DUT may be connected to an optical measurement instrument using a 1×N switch and a 1×M switch. The figure also shows the optics required for the re-calibration path. The three measurements across the re-calibration path are made at three different rotation states. This initial calibration configuration is shown in FIG. 18. These three measured matrices are used to generate the correction matrices as in the previously discussed calibration procedures.

$$BCA_S(\bar{M}_0, \bar{M}_1, \bar{M}_2) = \bar{S}' = \bar{A}^{-1} \bar{Q}^{-1} \bar{R}_{AQ} \tag{53}$$

and $$BCA_D(\bar{M}_0, \bar{M}_1, \bar{M}_2) = \bar{D}' = \bar{R}_{VB} \bar{V}^{-1} \bar{B}^{-1} \tag{54}$$

The next step is to measure a calibration device connected from source port 0 to detector port zero. The calibration device is measured at three different polarization states to produce, $\bar{M}_4$, $\bar{M}_5$ and $\bar{M}_6$. These measurements are corrected using $\bar{S}'$ and $\bar{D}'$, $$\bar{M}_3^c = \bar{D}' \bar{M}_4 \bar{S}' = (\bar{R}_{VB} \bar{V}^{-1} \bar{B}^{-1})(\bar{B}\bar{K}_0 \bar{R}_4 \bar{J}_0 \bar{A})(\bar{A}^{-1} \bar{Q}^{-1} \bar{R}_{AQ}) = \bar{R}_{VB} \bar{V}^{-1} \bar{K}_0 \bar{R}_4 \bar{J}_0 \bar{Q}^{-1} \bar{R}_{AQ} \tag{55}$$

$$\bar{M}_4^c = \bar{D}' \bar{M}_5 \bar{S} = (\bar{R}_{VB} \bar{V}^{-1} \bar{B}^{-1})(\bar{B}\bar{K}_0 \bar{R}_5 \bar{J}_0 \bar{A})(\bar{A}^{-1} \bar{Q}^{-1} \bar{R}_{AQ}) = \bar{R}_{VB} \bar{V}^{-1} \bar{K}_0 \bar{R}_5 \bar{J}_0 \bar{Q}^{-1} \bar{R} \bar{R}_{AQ} \tag{56}$$

$$\bar{M}_5^c = \bar{D}' \bar{M}_6 \bar{S} = (\bar{R}_{VB} \bar{V}^{-1} \bar{B}^{-1})(\bar{B}\bar{K}_0 \bar{R}_6 \bar{J}_0 \bar{A})(\bar{A}^{-1} \bar{Q}^{-1} \bar{R}_{AQ}) = \bar{R}_{VB} \bar{V}^{-1} \bar{K}_0 \bar{R}_6 \bar{J}_0 \bar{Q}^{-1} \bar{R}_{AQ} \tag{57}$$

These three matrices are then used in the Basic Calibration Algorithm to calculate the Source and Detector correction matrices for the source port 0 and the detector port 0.

$$BCA_S(\bar{M}_3^c, \bar{M}_4^c, \bar{M}_5^c) = \bar{S}''_0 = \bar{R}_{AQ}^{-1} \bar{Q} \bar{J}_0^{-1} \bar{R}_{j0} \tag{58}$$

and $$BCA_D(\bar{M}_3^c, \bar{M}_4^c, \bar{M}_5^c) = \bar{D}''_0 = \bar{R}_{K0}^{-1} \bar{K}_0^{-1} \bar{V} \bar{R}_{VB}^{-1} \tag{59}$$

If a calibration path (e.g., an optical fiber patch cord), such as shown in FIG. 18, from source port zero to detector port m, we will measure, $$\bar{M}_{0m} = \bar{B} \bar{K}_m \bar{R}_{0m} \bar{J}_0 \bar{A} \tag{60}$$

From this single matrix measurement, we can calculate the correction matrix for the mth detection port, $\bar{R}''_m$, to be $$\bar{D}''_m = \bar{S}''_0{}^{-1} \bar{S}'^{-1} \bar{M}_{0m}{}^{-1} \bar{D}'^{-1} = (\bar{R}_{j0} \bar{J}_0 \bar{Q}_{AQ})(\bar{R}_{AQ}{}^{-1} \bar{Q} \bar{A})(\bar{A}^{-1} \bar{J}_0{}^{-1} \bar{R}_{0m}{}^{-1} \bar{K}_m{}^{-1} \bar{B}^{-1})(\bar{B} \bar{V} \bar{R}_{VB}{}^{-1}) = \bar{R}_{j0} \bar{R}_{0m}{}^{-1} \bar{K}_m{}^{-1} \bar{V} \bar{R}_{VB}{}^{-1} \tag{61}$$

Following this procedure of connecting the calibration path to each detector port from the source port 0, we can the find the correction matrix for all M detector ports.

Figure 20:
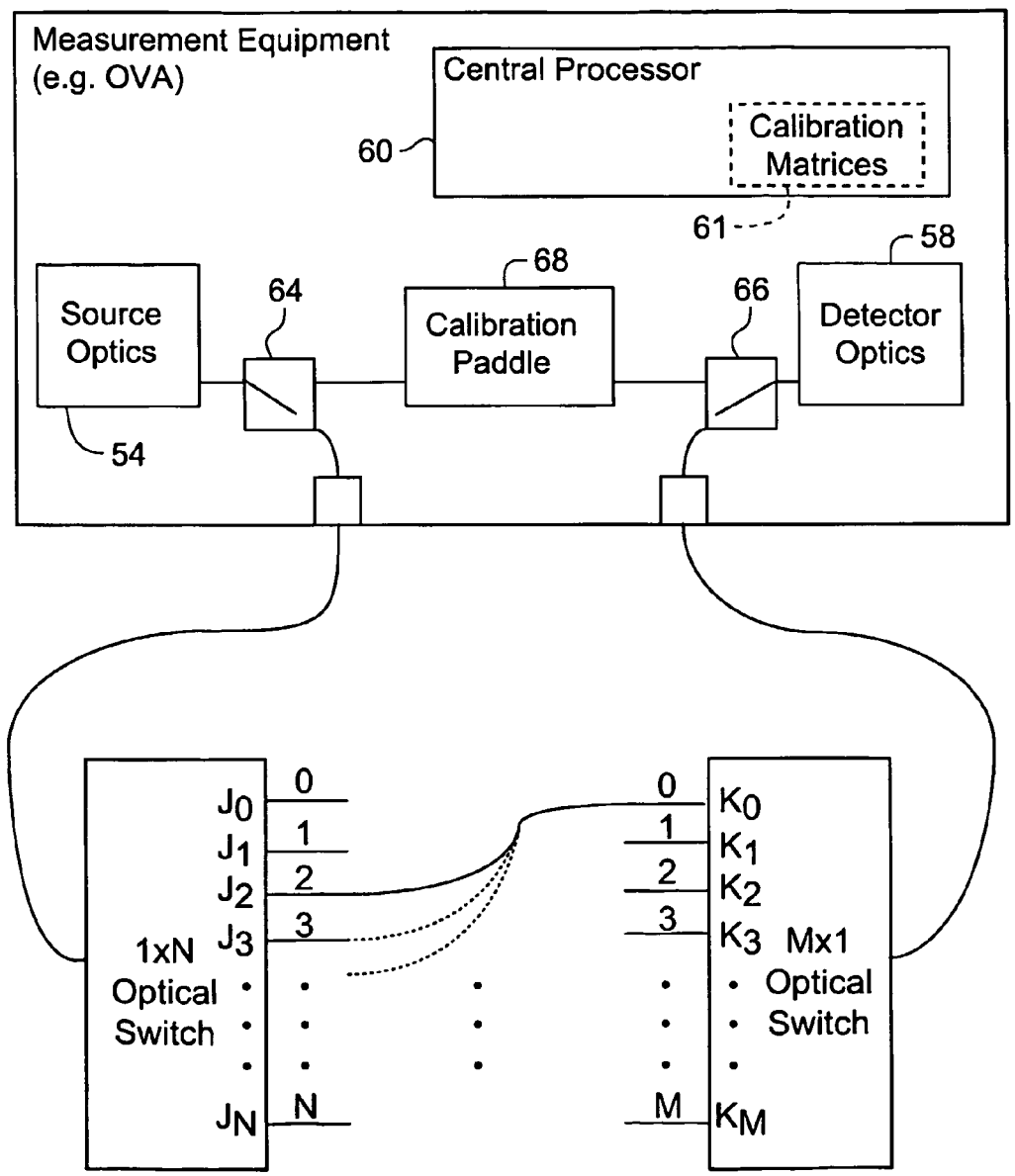
FIG. 20 illustrates a multi-channel measurement system constructed by connecting the 1×N and 1×M switches to an optical measurement system with a calibration device connected between source port n and detector port 0 for the third step in the calibration.

If a calibration path is created from source port n to detector port zero, as shown in FIG. 20, we will measure:

$$\bar{M}_{n0} = \bar{B} \bar{K}_0 \bar{R}_{n0} \bar{J}_n \bar{A} \tag{62}$$

From this single matrix measurement, we can calculate the correction matrix for the nth source port to be:

$$\overline{S}'''_n = \overline{S}'^{-1}\overline{M}_{n0}\overline{D}'^{-1}\overline{D}''_0^{-1} = (\overline{R}_{AQ}^{-1}\overline{QA})(\overline{A}^{-1}\overline{J}_n^{-1}\overline{R}_{0n}^{-1}$$
$$\overline{R}_0^{-1}\overline{B}^{-1})(\overline{BVR}_{VB}^{-1})(\overline{R}_{VB}\overline{V}^{-1}\overline{R}_0\overline{R}_{k0}^{-1}) = \overline{R}_{AQ}^{-1}\overline{Q}$$
$$\overline{J}_n^{-1}\overline{R}_{0n}^{-1}\overline{R}_{k0}^{-1} \quad (63)$$

We can then calculate total source and detector correction matrices for each port:

$$\overline{S}'''_n = \overline{S}'\overline{S}''_n = (\overline{A}^{-1}\overline{Q}^{-1}\overline{R}_{AQ})(\overline{R}_{AQ}^{-1}\overline{Q}\overline{J}_n^{-1}\overline{R}_{0n}^{-1}\overline{R}_{k0}^{-1}) =$$
$$\overline{A}^{-1}\overline{J}_n^{-1}\overline{R}_{0n}^{-1}\overline{R}_{k0}^{-1} \quad (64)$$

and $$\overline{D}'''_n = \overline{D}''_n\overline{D}' = (\overline{V}R_{VB}^{-1})(\overline{R}_{VB}\overline{V}^{-1}\overline{B}^{-1}) = \overline{R}_{j0}\overline{R}_{0m}^{-1}\overline{R}_m^{-1}$$
$$\overline{B}^{-1}. \quad (65)$$

Significantly, a substantial reduction is achieved in required calibration measurements. For example, a 40×40 switch requires only 3+39+39=81 measurements instead of the anticipated 3+3(39+39)=237 measurements.

An example calibration procedure for a multi-port/multi-channel device may include the following steps:

1—Perform a re-calibration of the measurement equipment through the re-calibration path.

$$BCA_S(\overline{M}_0, \overline{M}_1, \overline{M}_2) = \overline{S}' \quad (66)$$

and $$BCA_D(\overline{M}_0, \overline{M}_1, \overline{M}_2) = \overline{D}'' \quad (67)$$

2—Connect a lossless fiber containing an adjustable lossless matrix (like a loop paddle) between source port 0 and receiver port 0 as shown in FIG. 21.

3—Determine measurement matrices, $\overline{M}_3$, $\overline{M}_4$, and $\overline{M}_5$, through the source port 0 to receiver port 0 path at three different states of the adjustable lossless matrix. These measurements are corrected using $\overline{S}'$ and $\overline{D}'$, to produce $\overline{M}_3^c$, $\overline{M}_4^c$, and $\overline{M}_5^c$, as shown below $$\overline{M}_3^c = \overline{D}'\overline{M}_3\overline{S}' \quad (68)$$

$$\overline{M}_4^c = \overline{D}'\overline{M}_4\overline{S}' \quad (69)$$

$$\overline{M}_5^c = \overline{D}'\overline{M}_5\overline{S}' \quad (70)$$

4—Calculate the $\overline{S}''_0$, and $\overline{D}''_0$ matrices using the three matrices, $\overline{M}_3^c$, $\overline{M}_4^c$, and $\overline{M}_5^c$ measured in step 3, and the Basic Calibration Algorithm, $$BCA_S(\overline{M}_3^c, \overline{M}_4^c, \overline{M}_5^c) = \overline{S}'' \quad (71)$$

and $$BCA_D(\overline{M}_3^c, \overline{M}_4^c, \overline{M}_5^c) = \overline{D}'' \quad (72)$$

5—Disconnect the lossless fiber from receiver port 0 and connect it to receiver port m, and measure a lossless matrix, $\overline{M}_{0m}$ from the source 0 to the receiver port m. Repeat for every receiver port 1 to M 6—Reconnect the lossless fiber to receiver port 0.

7—Disconnect the lossless fiber from source 0 and connect the lossless fiber to source port n, measure a lossless matrix, $\overline{M}_{n0}$, from source port n to detector port 0. Repeat for source ports 1 to N, where N is the number of source ports to be calibrated.

8—From these measurements, calculate a correction matrix for each source and detector port.

$$\overline{S}''_n = \overline{S}'^{-1}\overline{M}_{n0}^{-1}\overline{D}'^{-1}\overline{D}''_0^{-1} \quad (73)$$

$$\overline{D}''_n = \overline{S}''_0^{-1}\overline{S}'^{-1}\overline{M}_{0m}^{-1}\overline{D}'^{-1} \quad (74)$$

Note that $\overline{S}'$ and $\overline{D}'$ were each determined in step 1, and $\overline{S}''_0$ and $\overline{D}''_0$ were determined in step 4.

8—Calculate a total correction matrix for each source and detector port $$\overline{S}'''_n = \overline{S}'\overline{S}''_n \quad (75)$$

$$\overline{D}'''_n = \overline{D}''_n\overline{D}' \quad (76)$$

9—If drift occurs in the Internal Source Optics, or the Internal Detector optics, Repeat steps 1 and 9 only to produce a new set of correction matrices, $$\overline{S}'''_{n,drift} = \overline{S}'_{drift}\overline{S}''_n \quad (77)$$

$$\overline{D}'''_{n,drift} = \overline{D}''_n\overline{D}'_{drift} \quad (78)$$

One advantage of the multi-port calibration described above is accurate measurement of multiple port devices using a set of switches, even if the switches have significant PDL. A second advantage, given the large time investment in calibrating large number of ports, is that each channel can be re-calibrated without reconnecting the lossless calibration device to each port. A third advantage is that by devising a way to find all but the first two port calibration matrices in a single measurement, (as opposed to the three rotation positions required for the first two), the most efficient calibration process possible is obtained.

While the description includes various example embodiments, it is to be understood that the claims are not to be limited to the disclosed example embodiments. On the contrary, the claims are intended to cover various other embodiments, implementations, modifications, and equivalent arrangements.

I claim:

1. A method for calibrating an apparatus for measuring one or more characteristics of an optical element, comprising the following steps:
    (a) providing a calibration path for the apparatus;
    (b) performing a calibration operation using the calibration path, wherein the calibration operation may be performed without the optical element having to be operatively de-coupled from the apparatus; and
    (c) calibrating the apparatus based on the calibration operation during a time period when the optical element is operatively coupled to the apparatus,
    wherein the calibration path includes a fiber loop polarization controller that remains in the calibration path even when the optical element under test is coupled to the apparatus;
    (d) moving the polarization controller to multiple positions;
    (e) determining one or more calibration corrections for the apparatus at each of the multiple positions of the polarization controller; and
    (f) using the one or more calibration corrections to update the calibration.

2. The method in claim 1, wherein the calibrating includes determining a source correction matrix that corrects for an affect of one or more components coupled between a light source in the apparatus and the source connector and determining a detector correction matrix that corrects for an affect of one or more components coupled between a light detector in the apparatus and the detector connector, and
    wherein the calibration operation includes determining an optical transfer function through the fiber loop polarization controller at multiple positions and determining the source correction matrix and the detector correction matrix using the optical transfer functions determined at each of the multiple positions.

3. The method in claim 1, further comprising:
performing another calibration operation using another calibration path with the optical element operatively dc-coupled from the apparatus and with a calibration component operatively coupled to the apparatus.

4. The method in claim 1, wherein the optical element is a device that is tested after calibrating the apparatus.

5. Apparatus for measuring one or more characteristics of optical element, comprising:
a source connector and a detector connector to which the optic element is coupled to measure the one or more characteristics;
a calibration path;
calibration circuitry configured to perform a calibration operation using the calibration path, wherein the calibration operation may be performed without the optical element having to be operatively de-coupled from the apparatus; and
processing circuitry configured to calibrate the apparatus based on the calibration operation during a time period when the optical element is operatively coupled to the apparatus,
wherein the calibration path includes a fiber loop polarization controller that remains in the calibration path even when the optical element under test is coupled to the apparatus,
wherein the processing circuitry is configured to:
move the polarization controller to multiple positions;
determine one or more calibration corrections for apparatus at each of the multiple positions of the polarization controller; and
use the one or more calibration corrections to update the calibration.

6. The apparatus in claim 5, wherein the processing circuitry is configured to:
determine a source correction matrix that corrects for an affect of components coupled between a light source in the apparatus and the source;
determine a detector correction matrix that corrects for an affect of components coupled between a light detector in the apparatus and the detector connector; and
determine an optical transfer function through the fiber loop polarization controller at multiple positions mad determining the source correction matrix and the detector correction matrix using the optical transfer functions determined at each of the multiple positions.

7. The apparatus in claim 5, wherein the processing circuitry is configured to perform another calibration operation using another calibration path with the optical element operatively de-coupled from the apparatus and with a calibration component operatively coupled to the apparatus.

8. The apparatus in claim 5, wherein the optical element is a device that is tested after calibrating the apparatus.

* * * * *